United States Patent
Peoples et al.

(10) Patent No.: US 8,097,709 B2
(45) Date of Patent: Jan. 17, 2012

(54) MACROLACTAM COMPOUNDS

(75) Inventors: Aaron Peoples, Cambridge, MA (US); Qibo Zhang, Albany, NY (US); Charles Moore, Boston, MA (US); Lucy Ling, Arlington, MA (US); Mithra Rothfeder, Belmont, MA (US); Kim Lewis, Newton, MA (US)

(73) Assignee: Novobiotic Pharmaceuticals, Inc., Cambridge, MA (US)

( * ) Notice: Subject to any disclaimer, the term of this patent is extended or adjusted under 35 U.S.C. 154(b) by 670 days.

(21) Appl. No.: 12/196,714

(22) Filed: Aug. 22, 2008

(65) Prior Publication Data
US 2009/0156514 A1 Jun. 18, 2009

Related U.S. Application Data

(60) Provisional application No. 60/965,748, filed on Aug. 22, 2007, provisional application No. 60/997,590, filed on Oct. 4, 2007, provisional application No. 61/035,886, filed on Mar. 12, 2008, provisional application No. 61/036,229, filed on Mar. 13, 2008, provisional application No. 61/045,784, filed on Apr. 17, 2008.

(51) Int. Cl.
*C07H 17/02* (2006.01)
*A01N 43/04* (2006.01)
*A61K 31/70* (2006.01)

(52) U.S. Cl. .......................... 536/17.4; 536/28
(58) Field of Classification Search .................. None
See application file for complete search history.

(56) References Cited

U.S. PATENT DOCUMENTS

| | | | |
|---|---|---|---|
| 4,904,644 | A | 2/1990 | Hedge et al. |
| 5,565,561 | A | 10/1996 | Muller et al. |
| 7,011,957 | B2 | 3/2006 | Lewis et al. |
| 2003/0059867 | A1 | 3/2003 | Lewis et al. |

OTHER PUBLICATIONS

Vippagunta et al. Advanced Drug Delivery Reviews 48 (2001) 3-26.*
Pollack. Rising Threat of Infections Unfazed by Antibiotics, The New York Times, Feb. 27, 2010.*
Fox. Nature Biotechnology, vol. 24, No. 12, Dec. 2006, pp. 1521-1528.*
MayoClinic.com—Bacterial infection vs. viral infection, Oct. 13, 2009.*
de Araujo, Janete M. et al., Isolation of Endophytic Actinomycetes from Roots and Leaves of Maize (Zea mays L.), Brazilian Archives of Biology and Technology, 2000, vol. 43, No. 4, pp. 447-451.
International Search Report and Written Opinion, International Application No. PCT/US08/74034, Dec. 18, 2008, 9 pages.
Borra, "Substrate Specificity and Kinetic Mechanism of the SIR2 Family of NAD+-Dependent Histone/Protein Deacetylases," Biochem. 43(30):9877-9887 (2004).
Gerber, et al., "Cell-Based Screen of HMG-CoA Reductase Inhibitors and Expression Regulators Using LC-MS," Anal. Biochem., 329:28-34 (2004).
Itoh, et al., "A Modified Method of Mixed Lymphocyte Reaction: Establishment of the Assay System and its Application to Extracts of Fungal Cultures," J. Antibiot. (Tokyo), 46(10):1575-81 (1993).
Roomi, et al., "Anti-Angiogenic Effects of a Nutrient Mixture on Human Umbilical Vein Endothelial Cells," Oncol. Rep., 14:1399-1404 (2005).
Johnson, et al., "Antioxidant With Marked Lipid-and Glucose-Lowering Activity in Diabetic Rats and Mice," Diabetes, 42:1179-1186 (1993).
Katiyar, et al., "Antiprotozoal Activities of Benzimidazoles and Correlations With Beta-Tubulin Sequence," Antimicrob. Agents Chemother., 38(9):2086-2090 (1994).
King, et al., Handbook of Organopalladium Chemistry for Organic Synthesis, John Wiley & Sons, Inc., 2:2719-2752 (2002).
Ndamba, et al., "Traditional Herbal Remedies Used for the Treatment of Urinary Schistosomiasis in Zimbabwe," J. Ethnopharmacol., 42:125-32 (1994).
Roomi, et al., "In Vivo and In Vitro Antitumor Effect of Ascorbic Acid, Lysine, Proline, Arginine, and Green Tea Extract on Human Fibrosarcoma Cells HT-1080," Med. Oncol. 23(1):105-112 (2006).
Sanati, et al., "A New Triazole, Voriconazole (UK-109,496), Blocks Sterol Biosynthesis in Candida Albicans and Candida Krusei," Antimicrob. Agents Chemother., 41(11): 2492-2496 (1997).
Singh, et al., "Development of an In Vitro Screening Assay to Test the Anti-Inflammatory Properties of Dietary Supplements and Pharmacologic Agents," Clin. Chem., 51(12):2252-2256 (2005).
Tisdale, "Monitoring of Viral Susceptibility: New Challenges With the Development of Influenza NA Inhibitors," Rev. Med. Virol., 10:45-55 (2000).
Yang, et al., Identification of Novel Human High-Density Lipoprotein Receptor Up-Regulators Using a Cell-Based High-Throughput Screening Assay, J. Biomol. Screen., 12(2):211-219 (2007).
Young, et al., "High-Throughput Screening With HyperCyt Flow Cytometry to Detect Small Molecule Formylpeptide Receptor Ligands," J. Biomol. Screen., 10(4):374-382 (2005).

* cited by examiner

*Primary Examiner* — Layla Bland
(74) *Attorney, Agent, or Firm* — K&L Gates LLP; Ann-Louise Kerner

(57) ABSTRACT

The invention relates generally to novel macrolactams and their analogs, to processes for the preparation of these novel macrolactams, to pharmaceutical compositions comprising the novel macrolactams; and to methods of using the novel macrolactams to treat or inhibit various disorders.

19 Claims, 4 Drawing Sheets

MACROLACTAM COMPOUNDS

CROSS-REFERENCES

This application claims the benefit of U.S. Provisional Patent Application Ser. Nos. 60/965,748 filed on Aug. 22, 2007 of Peoples, et al., entitled, "Glycosylated Macrolactam," 60/997,590 filed on Oct. 4, 2007 of Peoples, et al., entitled "Glycosylated Macrolactam," 61/035,886 filed on Mar. 12, 2008 of Peoples, et al., entitled "Novel Macrolactam Compounds," 61/036,229 filed on Mar. 13, 2008, of Peoples, et al., entitled "Novel Macrolactam Compounds," and 61/045,784 filed on Apr. 17, 2008 of peoples, et al., entitled "Novel Macrolactam Compounds." The entirety of these provisional patent applications are incorporated herein by reference.

STATEMENT REGARDING FEDERALLY SPONSORED RESEARCH OR DEVELOPMENT

Part of the work leading to this invention was carried out with United States Government support provided under a grant from the National Science Foundation, Grant No. 5R44AI063616. Therefore, the U.S. Government has certain rights in this invention.

FIELD OF THE INVENTION

The invention is in the field of microbial chemistry. More specifically, the invention is directed in part to novel macrolactam compounds and their analogs. The invention further relates to methods of using these compounds to treat disorders.

BACKGROUND OF THE INVENTION

Among modern medicine's great achievements is the development and successful use of antimicrobials against disease-causing microbes. Antimicrobials have saved numerous lives and reduced the complications of many diseases and infections. However, the currently available antimicrobials are not as effective as they once were.

Over time, many microbes have developed ways to circumvent the anti-microbial actions of the known antimicrobials, and in recent years there has been a worldwide increase in infections caused by microbes resistant to multiple antimicrobial agents. With the increased availability and ease of global travel, rapid spread of drug-resistant microbes around the world is becoming a serious problem. In the community, microbial resistance can result from nosocomial acquisition of drug-resistant pathogens (e.g., methicillin resistant *Staphylococcus aureus* (MRSA), vancomycin resistant *Enterococci* (VRE)), emergence of resistance due to use of antibiotics within the community (e.g., pencillin- and quinolone-resistant *Neisseria gonorrheae*), acquisition of resistant pathogens as a result of travel (e.g., antibiotic-resistant *Shigella*), or as a result of using antimicrobial agents in animals with subsequent transmission of resistant pathogens to humans (e.g., antibiotic resistant *Salmonella*). Antibiotic resistance in hospitals has usually resulted from overuse of antibiotics and has been a serious problem with MRSA, VRE, and multi-drug resistant Gram-negative bacilli (MDR-GNB) (e.g., *Enterobacter, Klebsiella, Serratia, Citrobacter, Pseudomonas*, and *E. coli*). In particular, catheter-related blood stream infections by bacteria and skin and soft tissue infections (SSTIs) are becoming an increasing problem.

Bacteria, viruses, fungi, and parasites have all developed resistance to known antimicrobials. Resistance usually results from three mechanisms: (i) alteration of the drug target such that the antimicrobial agent binds poorly and thereby has a diminished effect in controlling infection; (ii) reduced access of the drug to its target as a result of impaired drug penetration or active efflux of the drug; and (iii) enzymatic inactivation of the drug by enzymes produced by the microbe. Antimicrobial resistance provides a survival advantage to microbes and makes it harder to eliminate microbial infections from the body. This increased difficulty in fighting microbial infections has led to an increased risk of developing infections in hospitals and other settings. Diseases such as tuberculosis, malaria, gonorrhea, and childhood ear infections are now more difficult to treat than they were just a few decades ago. Drug resistance is a significant problem for hospitals harboring critically ill patients who are less able to fight off infections without the help of antibiotics. Unfortunately, heavy use of antibiotics in these patients selects for changes in microbes that bring about drug resistance. These drug resistant bacteria are resistant to our strongest antibiotics and continue to prey on vulnerable hospital patients. It has been reported that 5 to 10 percent of patients admitted to hospitals acquire an infection during their stay and that this risk has risen steadily in recent decades.

In view of these problems, there is an increasing need for novel antimicrobials to combat microbial infections and the problem of increasing drug resistance. A renewed focus on antimicrobial drug discovery is critical as pathogens are developing resistance to available drugs.

Synthetic compounds have thus far failed to replace natural antibiotics and to lead to novel classes of broad-spectrum compounds, despite the combined efforts of combinatorial synthesis, high-throughput screening, advanced medicinal chemistry, genomics and proteomics, and rational drug design. The problem with obtaining new synthetic antibiotics may be related in part to the fact that the synthetic antibiotics are invariably pumped out across the outer membrane barrier of bacteria by Multidrug Resistance pumps (MDRs). The outer membrane of bacteria is a barrier for amphipathic compounds (which essentially all drugs are), and MDRs extrude drugs across this barrier. Evolution has produced antibiotics that can largely bypass this dual barrier/extrusion mechanism, but synthetic compounds almost invariably fail. There is not currently available a rational means to create compounds that will be both active and capable of penetrating into bacteria.

SUMMARY OF THE INVENTION

This application is directed to a novel macrolactam compound that is useful in the treatment of a number of disorders, including microbial infections.

In one aspect, the invention relates to compounds of formula I,

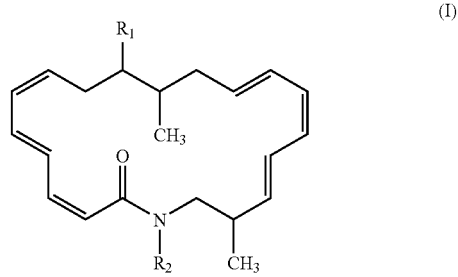

(I)

and enantiomers, diastereomers, tautomers, pharmaceutically-acceptable salts and solvates thereof, wherein $R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, (=O), OR$_a$, OC(=O)R$_a$, SR$_a$, S(=O)$_2$R$_d$, NR$_b$R$_c$ or sugar group; R$_2$ is hydrogen, NH$_2$, —OH, alkyl or substituted alkyl, cycloalkyl or substituted cycloalkyl; each R$_a$ is independently hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; R$_b$ and R$_c$ are each independently hydrogen, alkyl, substituted alkyl, cycloalkyl, substituted cycloalkyl, heterocycle, substituted heterocycle, aryl, substituted aryl, or said R$_b$ and R$_c$ together with the N to which they are bonded optionally form a heterocycle or substituted heterocycle; and each R$_d$ is independently alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl.

In certain embodiments of this aspect, R$_2$ is hydrogen. In certain other embodiments, R$_1$ is a sugar group. In some cases, the sugar group is a mono-, di- or poly-saccharide. In specific embodiments, the mono-, di- or poly-saccharides are L-rhamnose, L-fucose, D-perosamine, 6-deoxy-D-gulose, 6-deoxy-L-altrose, 6-deoxy-D-glucose, L-ascarylose, D-abequose, D-paratose, D-tyvelose, D-colitose, D-olivose, D-oliose, D- and L-mycarose, L-oleandrose, L-rhodinose, D-glucose, D-galactose, D-mannose, D-glucosamine, D-galactosamine, acetyl-D-glucosamine, L-daunosamine, D-desosamine, D-mycaminose, N-methyl-L-glucosamine, 4-acetamido-4,6-dideoxygalactose, D-mannosamine, neuraminic acid, or muramic acid. In some embodiments, the sugar is attached at any available O or N position. In other embodiments, the amino group of the sugar is optionally mono-methylated, di-methylated, or acetylated, and the hydroxyl group of the sugar is optionally methylated or acetylated.

In certain embodiments, the invention relates to compounds of the formula Ia

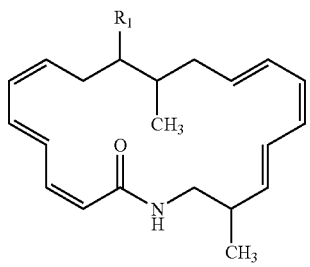

(Ia)

and enantiomers, diastereomers, tautomers, pharmaceutically-acceptable salts and solvates thereof, wherein R$_1$ is hydrogen, halogen, cyano, nitro, CF$_3$, OCF$_3$, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, (=O), OR$_a$, OC(=O)R$_a$, SR$_a$, S(=O)$_2$R$_d$, NR$_b$R$_c$ or sugar group. In some cases, R$_1$ is a sugar group. In some other cases, the sugar group is a mono-, di- or poly-saccharide. Examples of mono-, di- or poly-saccharides include, but not limited to, L-rhamnose, L-fucose, D-perosamine, 6-deoxy-D-gulose, 6-deoxy-L-altrose, 6-deoxy-D-glucose, L-ascarylose, D-abequose, D-paratose, D-tyvelose, D-colitose, D-olivose, D-oliose, D- and L-mycarose, L-oleandrose, L-rhodinose, D-glucose, D-galactose, D-mannose, D-glucosamine, D-galactosamine, acetyl-D-glucosamine, L-daunosamine, D-desosamine, D-mycaminose, N-methyl-L-glucosamine, 4-acetamido-4,6-dideoxygalactose, D-mannosamine, neuraminic acid, or muramic acid. In certain embodiments, the sugar is attached at any available O or N position. In other embodiments, the amino group of the sugar is optionally mono-methylated, di-methylated, or acetylated, and the hydroxyl group of the sugar is optionally methylated or acetylated.

In some embodiments, the invention relates to compounds having the structure of Ib

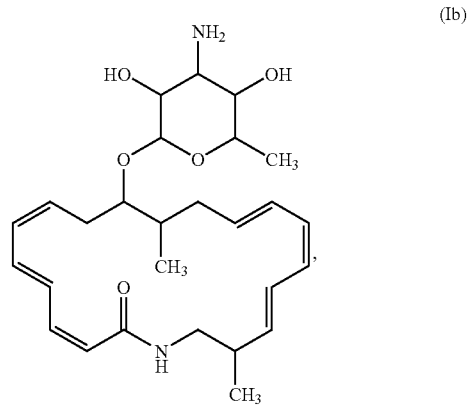

(Ib)

and enantiomers, diastereomers, tautomers, pharmaceutically-acceptable salts and solvates thereof, wherein the amino group is optionally mono-methylated, di-methylated, or acetylated, and the hydroxyl group is optionally methylated or acetylated.

In yet another aspect, the invention relates to compounds of formula II,

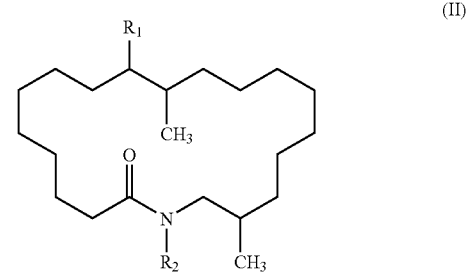

(II)

and enantiomers, diastereomers, tautomers, or pharmaceutically-acceptable salts or solvates thereof, wherein R$_1$ is hydrogen, halogen, cyano, nitro, CF$_3$, OCF$_3$, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, (=O), OR$_a$, OC(=O)R$_a$, SR$_a$, S(=O)$_2$R$_d$, NR$_b$R$_c$ or sugar groups (including amino sugar and mono-, di- or poly-saccharides); R$_2$ is hydrogen, NH$_2$, —OH, alkyl, substituted alkyl, cycloalkyl, or substituted cycloalkyl; each R$_a$ is independently hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl; R$_b$ and R$_c$ are each independently hydrogen, alkyl, substituted alkyl, cycloalkyl, substituted cycloalkyl, heterocycle, substituted heterocycle, aryl, substituted aryl, or said $R_b$ and $R_c$ together with the N to which they are bonded optionally form a heterocycle or substituted heterocycle; and each $R_d$ is independently alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl.

In certain embodiments of this aspect, $R_2$ is hydrogen. In other embodiments, $R_1$ is a sugar group. In some cases, the sugar group is a mono-, di- or poly-saccharide. In specific embodiments, mono-, di- or poly-saccharides are L-rhamnose, L-fucose, D-perosamine, 6-deoxy-D-gulose, 6-deoxy-L-altrose, 6-deoxy-D-glucose, L-ascarylose, D-abequose, D-paratose, D-tyvelose, D-colitose, D-olivose, D-oliose, D- and L-mycarose, L-oleandrose, L-rhodinose, D-glucose, D-galactose, D-mannose, D-glucosamine, D-galactosamine, acetyl-D-glucosamine, L-daunosamine, D-desosamine, D-mycaminose, N-methyl-L-glucosamine, 4-acetamido-4,6-dideoxygalactose, D-mannosamine, neuraminic acid, or muramic acid. In certain embodiments, the sugar is attached at any available O or N position. In certain other embodiments, the amino group of the sugar is optionally mono-methylated, di-methylated, or acetylated, and the hydroxyl group of the sugar is optionally methylated or acetylated.

In certain embodiments, the invention relates to compounds having the structure of IIa:

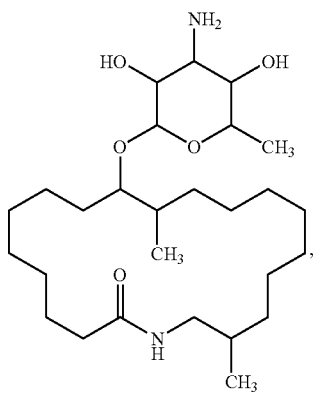

(IIa)

and enantiomers, diastereomers, tautomers, pharmaceutically-acceptable salts and solvates thereof, wherein the amino group is optionally mono-methylated, di-methylated, or acetylated, and the hydroxyl group is optionally methylated or acetylated.

In another aspect, the invention relates to a compound characterized by having a molecular weight of about 472.62 g/mol; a proton nuclear magnetic resonance spectrum substantially the same as that shown in FIG. 1; and a COSY nuclear magnetic resonance spectrum substantially the same as that shown in FIG. 2. In certain embodiments, the invention relates to a compound characterized by having a molecular weight of about 472.62 g/mol, and a proton nuclear magnetic resonance spectrum substantially the same as that shown in Table 1. In certain other embodiments, the invention relates to a compound characterized by having a molecular weight of about 472.62 g/mol, and to the acylated analog of the compound having a carbon-13 nuclear magnetic resonance spectrum substantially the same as that shown in Table 1.

Aspects of the invention also relate to a pharmaceutical composition comprising at least one of the compounds described herein (e.g., compounds of formulae I, Ia, Ib, II, and IIa) and a pharmaceutically-acceptable excipient, carrier, or diluent. In certain embodiments, the composition further comprises a therapeutic agent selected from the group consisting of an anti-neoplastic agent, an antibiotic, an antifungal agent, an antiviral agent, an anti-protozoan agent, an anthelminthic agent, and combinations thereof.

In yet another aspect, the invention relates to a method for producing a compound of formula Ib:

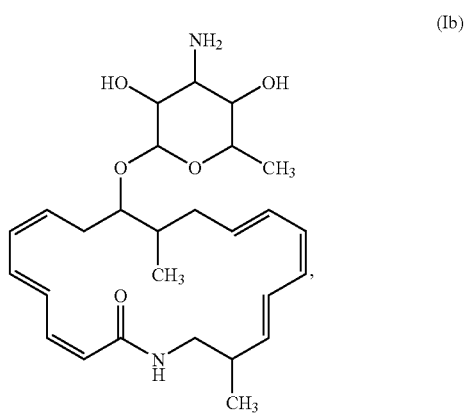

(Ib)

This method comprises cultivating a P1532 strain of *Streptosporangium* (ATCC Deposit No. PTA-8676) in a culture medium comprising assimilable sources of carbon, nitrogen, and inorganic salts under aerobic conditions enabling the production of an assayable amount of the compound of formula (Ib). In certain embodiments, the process further comprises isolating the compound of formula (Ib).

In yet another aspect, the invention relates to a compound of formula (Ib) prepared by the process described supra.

In still another aspect, the invention relates to a method of treating a disorder in a subject in need thereof, wherein the disorder is caused by a bacterium, a fungus, a virus, a protozoan, a helminth, a parasite, or combinations thereof, the method comprising administering to the subject a therapeutically effective amount of a compound described herein.

In yet another aspect, the invention relates to a method of treating a disorder in a subject in need thereof, wherein the disorder is a cardiovascular disease, hypercholesterolemia (e.g., decreased HDL levels, increased LDL levels), an inflammatory disorder, an aging-related disease, a channelopathy, an autoimmune disease, a graft versus host disease, a cancer, or combinations thereof, the method comprising administering to the subject a therapeutically effective amount of a macrolactam compound described herein. In certain embodiments, the invention envisions use of a second agent, wherein the second agent is known to be useful in the treatment of the disorder. In a specific embodiment, where the disorder is cancer, the second agent may be a chemotherapeutic agent.

In yet another aspect, the invention relates to a method of inhibiting the growth of an infective agent, the method comprising contact of the agent with a compound described herein. The method inhibits the growth of the infective agent compared with the growth of the infective agent in the absence of contacting the agent with a compound of the invention. In some embodiments, the infective agent is selected from the group consisting of a bacterium, a fungus, a virus, a protozoan, a helminth, a parasite, and combinations thereof. The method may be practiced in vivo or in vitro.

In yet another aspect, the invention relates to an isolated culture comprising a *Streptosporangium* species, having the identifying characteristics of a P1532 strain with the designation ATCC® NO. PTA-8676.

DESCRIPTION OF THE FIGURES

The foregoing and other objects of the present invention, the various features thereof, as well as the invention itself may be more fully understood from the following description, when read together with the accompanying drawings in which.

DETAILED DESCRIPTION OF THE INVENTION

Figure 1:
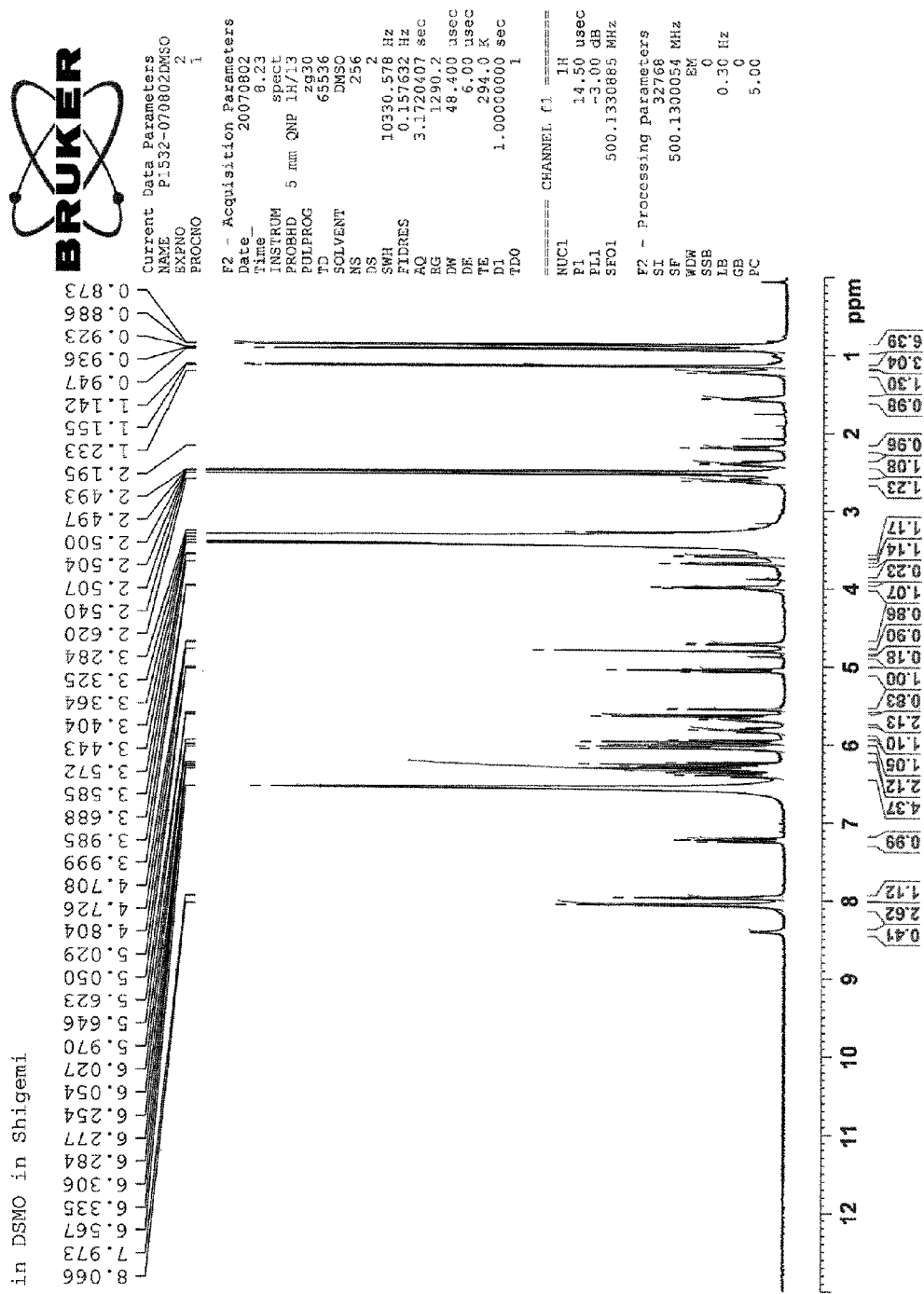
FIG. 1 is a representation of proton nuclear magnetic resonance spectrum of a compound isolated from a growing strain of *Streptosporangium*.

The invention relates generally to novel macrolactams and their analogs, to processes for the preparation of these novel macrolactams, to pharmaceutical compositions comprising the novel macrolactams, and to methods of using the novel macrolactams to treat or inhibit various disorders.

Throughout this application, various patents, patent applications, and publications are referenced. The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "about" is used herein to mean a value − or +20% of a given numerical value. Thus, about 60% means a value of between 60%−20% of 60 and 60%+20% of 60 (i.e., between 48% and 72%).

The term "substantially the same" is used herein to mean that two comparing subjects share at least 90% of common feature. In certain embodiments, the common feature is at least 95%. In certain other embodiments, the common feature at least 99%.

The term "isolated" is used herein to mean purified to a state beyond that in which it exists in nature. For example an isolated compound can be substantially free of cellular material or other contaminating materials from the cell from which the compound is derived, or substantially free from chemical precursors or other chemicals when chemically synthesized. In some embodiments, the preparation of a compound having less than about 50% (by dry weight) of contaminating materials from the cell, or of chemical precursors is considered to be substantially pure. In other embodiments, the preparation of a compound having less than about 40%, about 30%, about 20%, about 10%, about 5%, about 1% (by dry weight) of contaminating materials from the cell, or of chemical precursors is considered to be substantially pure.

The terms "alkyl" and "alk" refers to a straight or branched chain alkane (hydrocarbon) radical containing from 1 to 12 carbon atoms, e.g., 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, e.g. 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$, cyano, nitro, $CF_3$, $OCF3$, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_aC(=O)NR_bR_c$, $NR_aS(=O)_2NR_bR_c$, $NR_dP(=O)_2NR_bR_c$, $NR_bC(=O)R_a$, or $NR_bP(=O)_2R_e$, wherein each $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle or substituted heterocycle; and each $R_e$ is alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, e.g., 1 to 4 substituents, at any available point of attachment. Exemplary substituents include, but are not limited to, alkyl or substituted alkyl, as well as those groups recited above as exemplary alkyl substituents. The exemplary substituents can themselves be optionally substituted.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, e.g., 1 to 4 substituents, at any available point of attachment. Exemplary substituents include, but are not limited to, alkyl or substituted alkyl, as well as those groups recited above as exemplary alkyl substituents. The exemplary substituents can themselves be optionally substituted.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, e.g., 1 to 4 substituents, at any available point of attachment. Exemplary substituents include, but are not limited to, nitro, cyano, alkyl or substituted alkyl, as well as those groups recited above as exemplary alkyl substituents. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, e.g., 1 to 4 substituents, at any available point of attachment. Exemplary substituents include but are not limited to nitro, cyano, alkyl or substituted alkyl, as well as those groups recited above as exemplary alkyl substituents. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, e.g., 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. The exemplary substituents can themselves be optionally substituted. Exemplary substituents also include fused cyclic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, e.g., 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. The exemplary substituents can themselves be optionally substituted. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The terms "halogen" and "halo" refer to chlorine, bromine, fluorine, or iodine.

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, e.g., 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents. The exemplary substituents can themselves be optionally substituted.

Unless otherwise indicated, any heteroatom with unsatisfied valences is assumed to have hydrogen atoms sufficient to satisfy the valences.

The term "heating" includes, but not limited to, warming by conventional heating (e.g., electric heating, steam heating, gas heating, etc.) as well as microwave heating.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient.

The term "NOVO3" is used herein to mean the compound of formula Ib:

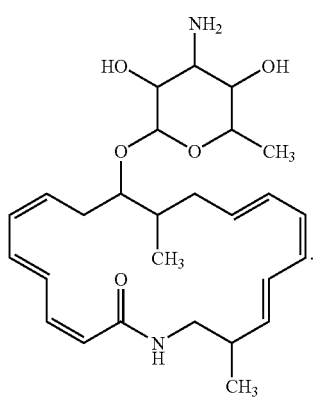

(Ib)

The term "treating" with regard to a subject, refers to improving at least one symptom of the subject's disorder. Treating can be curing the disorder or condition, or improving it.

The term "disorder" is used herein to mean, and is used interchangeably with, the terms disease, condition, or illness, unless context clearly indicates otherwise.

The term "microbe" is used herein to mean an organism such as a bacterium, a virus, a protozoan, or a fungus, especially one that transmits disease.

The phrase "effective amount" as used herein means that amount of one or more agent, material, or composition comprising one or more agents of the present invention that is effective for producing some desired effect in an animal. It is recognized that when an agent is being used to achieve a therapeutic effect, the actual dose which comprises the "effective amount" will vary depending on a number of conditions including, but not limited to, the particular condition being treated, the severity of the disease, the size and health of the patient, the route of administration. A skilled medical practitioner can readily determine the appropriate dose using methods well known in the medical arts.

The phrase "pharmaceutically acceptable" is employed herein to refer to those compounds, materials, compositions, and/or dosage forms which are, within the scope of sound medical judgment, suitable for use in contact with the tissues of human beings, animals and plants without excessive toxicity, irritation, allergic response, or other problem or complication, commensurate with a reasonable benefit/risk ratio.

Throughout the specifications, groups and substituents thereof may be chosen to provide stable moieties and compounds.

Compounds

In one aspect, the invention provides compounds of formula I,

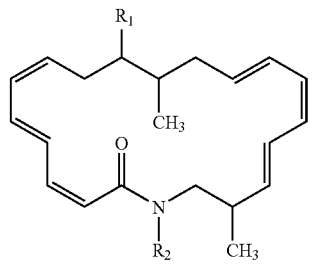

(I)

and enantiomers, diastereomers, tautomers, pharmaceutically-acceptable salts and solvates thereof, wherein $R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, (=O), $OR_a$, OC(=O) $R_a$, $SR_a$, $S(=O)_2R_d$, $NR_bR_c$ or sugar group. $R_2$ is hydrogen, $NH_2$, —OH, alkyl or substituted alkyl, cycloalkyl or substituted cycloalkyl, (preferably hydrogen). Each $R_a$ is independently hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl. $R_b$ and $R_c$ are each independently hydrogen, alkyl, substituted alkyl, cycloalkyl, substituted cycloalkyl, heterocycle, substituted heterocycle, aryl, substituted aryl, or $R_b$ and $R_c$ together with the N to which they are bonded optionally form a heterocycle or substituted heterocycle. Each $R_d$ is independently alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl.

In certain embodiments of this aspect, $R_2$ is hydrogen. In certain other embodiments, $R_1$ is a sugar group. In some cases, the sugar group is a mono-, di- or poly-saccharide. Examples of mono-, di- or poly-saccharides include, but not limited to, L-rhamnose, L-fructose, D-perosamine, 6-deoxy-D-gulose, 6-deoxy-L-altrose, L-ascarylose, D-abequose, D-paratose, D-tyvelose, D-colitose, D-olivose, D-oliose, D- and L-mycarose, L-oleandrose, L-rhodinose, D-glucose, D-galactose, D-mannose, D-glucosamine, D-galactosamine, acetyl-D-glucosamine, L-daunosamine, D-desosamine, D-mycaminose, N-methyl-L-glucosamine, 4-acetamido-4,6-dideoxygalactose, D-mannosamine, neuraminic acid, or muramic acid. In certain embodiments, the sugar is attached at any available O or N position. In certain other embodiments, the amino group of the sugar is optionally mono-methylated, di-methylated, or acetylated, and the hydroxyl group of the sugar is optionally methylated or acetylated.

In certain embodiments, the invention relates to compounds of formula Ia

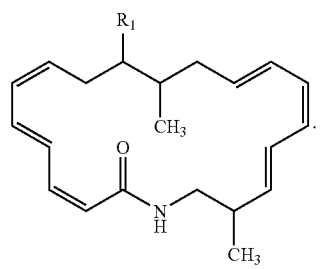

(Ia)

and enantiomers, diastereomers, tautomers, pharmaceutically-acceptable salts and solvates thereof, wherein, $R_1$ is hydrogen, halogen, cyano, nitro, $CF_3$, $OCF_3$, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, (=O), $OR_a$, $OC(=O)R_a$, $SR_a$, $S(=O)_2R_d$, $NR_bR_c$ or sugar group. In some cases, $R_1$ is a sugar group. In some other cases, the sugar group is a mono-, di- or poly-saccharide. Examples of mono-, di- or poly-saccharides include, but not limited to, L-rhamnose, L-fructose, D-perosamine, 6-deoxy-D-gulose, 6-deoxy-L-altrose, 6-deoxy-D-glucose, L-ascarylose, D-abequose, D-paratose, D-tyvelose, D-colitose, D-olivose, D-oliose, D- and L-mycarose, L-oleandrose, L-rhodinose, D-glucose, D-galactose, D-mannose, D-glucosamine, D-galactosamine, acetyl-D-glucosamine, L-daunosamine, D-desosamine, D-mycaminose, N-methyl-L-glucosamine, 4-acetamido-4,6-dideoxygalactose, D-mannosamine, neuraminic acid, or muramic acid. In certain embodiments, the sugar is attached at any available O or N position. In certain other embodiments, the amino group of the sugar is optionally mono-methylated, di-methylated, or acetylated, and the hydroxyl group of the sugar is optionally methylated or acetylated.

In certain embodiments, the invention relates to compounds having the structure of Ib

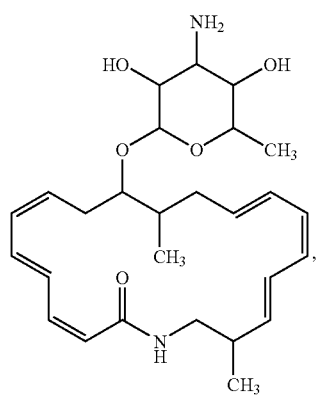

(Ib)

and enantiomers, diastereomers, tautomers, pharmaceutically-acceptable salts and solvates thereof, wherein the amino group is optionally mono-methylated, di-methylated, or acetylated, and the hydroxyl group is optionally methylated or acetylated.

In another aspect, the invention relates to compounds of formula II,

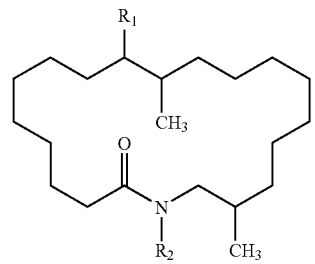

(II)

and enantiomers, diastereomers, tautomers, pharmaceutically-acceptable salts and solvates thereof, wherein $R_1$ is hydrogen, halogen, cyano, nitro, $CF_3$, $OCF_3$, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, (=O), $OR_a$, $OC(=O)R_a$, $SR_a$, $S(=O)_2R_d$, $NR_bR_c$ or sugar groups (including amino sugar and mono-, di- or poly-saccharides). $R_2$ is hydrogen, $NH_2$, —OH, alkyl, substituted alkyl, cycloalkyl, or substituted cycloalkyl. Each $R_a$ is independently hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl. $R_b$ and $R_c$ are each independently hydrogen, alkyl, substituted alkyl, cycloalkyl, substituted cycloalkyl, heterocycle, substituted heterocycle, aryl, substituted aryl, or $R_b$ and $R_c$ together with the N to which they are bonded optionally form a heterocycle or substituted heterocycle. Each $R_d$ is independently alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl.

In certain embodiments of this aspect, $R_2$ is hydrogen. In certain other embodiments, $R_1$ is a sugar group. In some cases, the sugar group is a mono-, di- or poly-saccharide. Examples of mono-, di- or poly-saccharides include, but not limited to, L-rhamnose, L-fructose, D-perosamine, 6-deoxy-D-gulose, 6-deoxy-L-altrose, 6-deoxy-D-glucose, L-ascarylose, D-abequose, D-paratose, D-tyvelose, D-colitose, D-olivose, D-oliose, D- and L-mycarose, L-oleandrose, L-rhodinose, D-glucose, D-galactose, D-mannose, D-glucosamine, D-galactosamine, acetyl-D-glucosamine, L-daunosamine, D-desosamine, D-mycaminose, N-methyl-L-glucosamine, 4-acetamido-4,6-dideoxygalactose, D-mannosamine, neuraminic acid, or muramic acid. In certain embodiments, the sugar is attached at any available O or N position. In certain other embodiments, the amino group of the sugar is optionally mono-methylated, di-methylated, or acetylated, and the hydroxyl group of the sugar is optionally methylated or acetylated.

In certain embodiments, the invention relates to a compound having the structure of IIa:

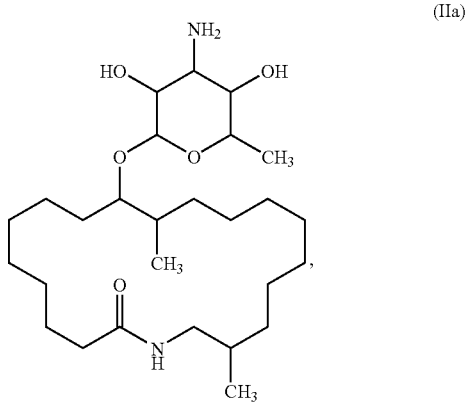

(IIa)

and enantiomers, diastereomers, tautomers, pharmaceutically-acceptable salts and solvates thereof, wherein the amino group is optionally mono-methylated, di-methylated, or acetylated, and the hydroxyl group is optionally methylated or acetylated.

Figure 2:
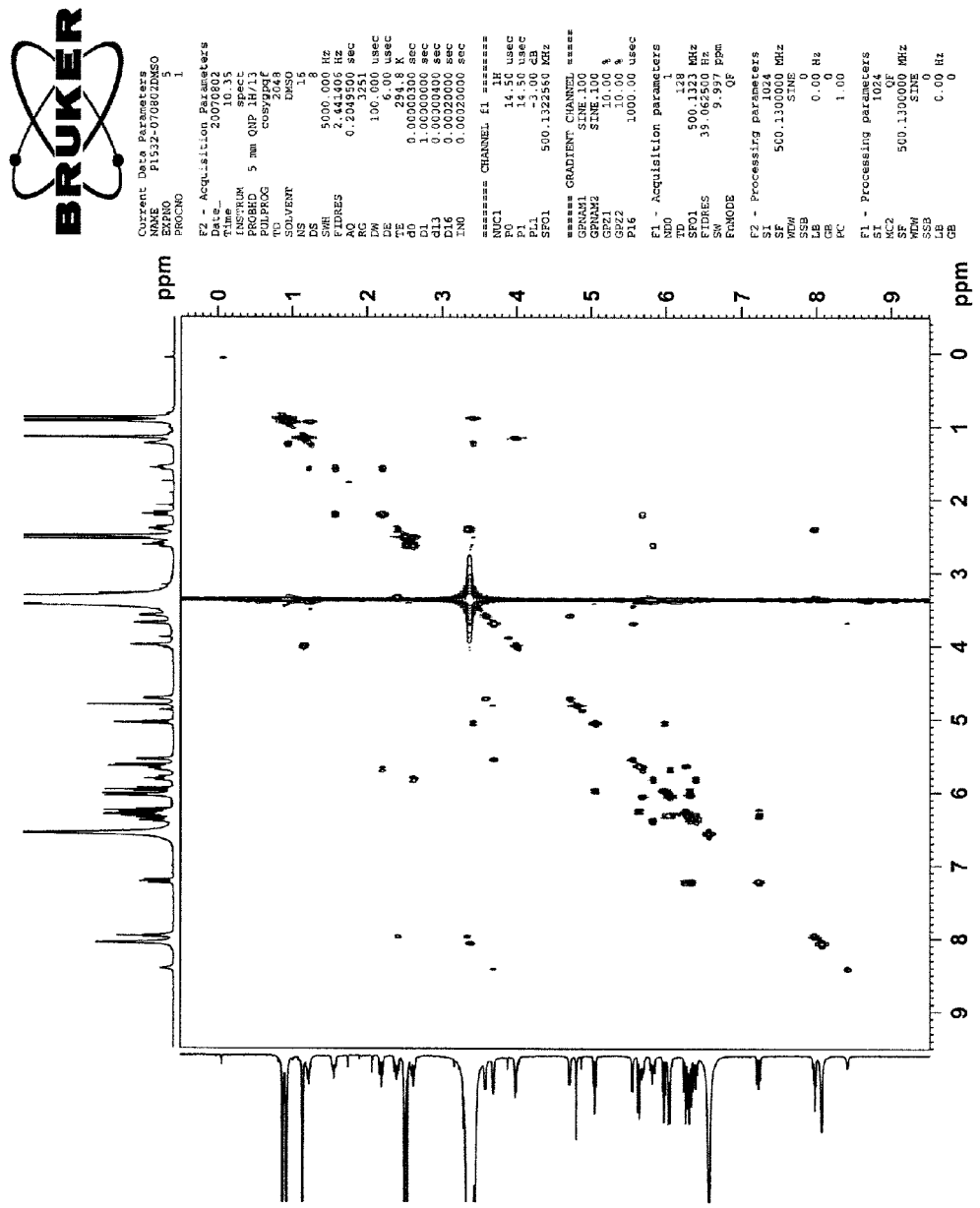
FIG. 2 is a representation of COSY nuclear magnetic resonance spectrum of a compound isolated from a growing strain of *Streptosporangium*.

In a further aspect, the invention relates to a compound characterized by having a molecular weight of 472.62 g/mol; a proton nuclear magnetic resonance spectrum substantially the same as that shown in FIG. 1; and a COSY nuclear magnetic resonance spectrum substantially the same as that shown in FIG. 2. In certain embodiments, the invention relates to a compound characterized by having a molecular weight of 472.62 g/mol, and a proton nuclear magnetic resonance spectrum substantially the same as that shown in Table 1. In certain other embodiments, the invention relates to a compound characterized by having a molecular weight of about 472.62 g/mol, and to the acylated analog of the compound having a carbon-13 nuclear magnetic resonance spectrum substantially the same as that shown in Table 1.

In another aspect, the invention relates to a pharmaceutical composition comprising the compounds described herein and a pharmaceutically-acceptable excipient, carrier, or diluent. In certain embodiments, the composition further comprises a therapeutic agent selected from the group consisting of an anti-neoplastic agent, an antibiotic, an antifungal agent, an antiviral agent, an anti-protozoan agent, an anthelminthic agent, and combinations thereof.

In yet another aspect, the invention relates to a process for production of a compound of formula Ib:

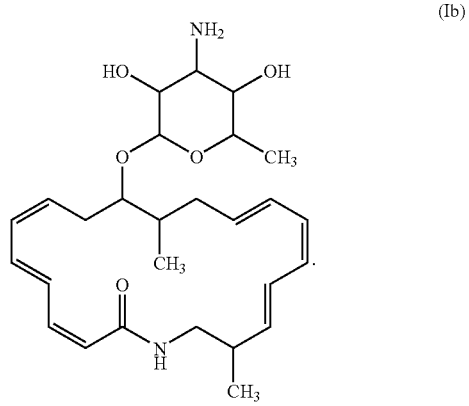

(Ib)

The process comprises cultivating a P1532 strain of *Streptosporangium* (ATCC® Deposit No. PTA-8676) in a culture medium comprising assimilable sources of carbon, nitrogen, and inorganic salts under aerobic conditions enabling the production of an assayable amount of the compound of formula (Ib). In certain embodiments, the process further comprises isolating the compound of formula (Ib).

In yet another aspect, the invention relates to a compound of formula (Ib) prepared by the processes described below.

The macrolactam compounds of the present invention may form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I or II with an amount of acid or base, such as an equivalent amount, in a medium such as one in which the salt precipitates or in an aqueous medium followed by lyophilization.

The macrolactam compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The macrolactam compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the macrolactam compounds of the invention are also contemplated herein. Solvates of the compounds of the present invention include, for example, hydrates.

Macrolactam compounds of the present invention, and salts thereof, may exist in their tautomeric form (for example, as an amide or imino ether). All such tautomeric forms are contemplated herein as part of the present invention.

All stereoisomers of the macrolactam compounds of the present invention (for example, those which may exist due to asymmetric carbons on various substituents), including enantiomeric forms and diastereomeric forms, are contemplated within the scope of this invention. Individual stereoisomers of the macrolactam compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Macrolactam compounds of the present invention are, subsequent to their preparation, e.g., isolated and purified to obtain a composition containing an amount by weight equal to or greater than 99% ("substantially pure" compound I), which is then used or formulated as described herein.

All configurational isomers of the compounds of the present invention are contemplated either in admixture or in pure or substantially pure form. The definition of compounds of the present invention embraces both cis (z) and trans (E) alkene isomers, as well as cis and trans isomers of cyclic hydrocarbon or heterocyclic rings.

Methods of Preparation

NOVO3 is produced by the P1532 isolate that is deposited with the American Type Culture Collection (ATCC®) at 10801 University Boulevard, Manassas, Va. 20110-2209, USA as PTA-8676 under the provisions of the Budapest Treaty.

The P1532 isolate was obtained from soil collected from a fallow corn field in New York using the technology for isolating "unculturable" microorganisms described in U.S. Pat. No. 7,011,957. This technology makes use of a growth chamber that is sealed with a semi-permeable membrane, and thus is permeable to diffusion of components from the environment but not to cells of microorganisms.

The growth chamber is designed to allow for the growth, isolation into pure culture, and characterization of microorganisms that are "uncultivable" at the present time. This desired result can be achieved because the conditions inside the chamber closely resemble, if they are not identical to, the natural environment of the microorganisms. One version of such a chamber is formed from a solid substrate, e.g., a glass or silicon slide or stainless steel washer, having an orifice which is sandwiched by two robust membranes, e.g., polycarbonate or other inert material, glued onto the substrate. The membranes have pore sizes, e.g., 0.025 µm-0.03 µm, that are sufficiently small to retain all microorganisms inside the chamber but which are sufficiently large to permit components from the environment to diffuse into the chamber and waste products to diffuse out of the chamber. After one membrane is sealed onto the bottom of the substrate, the chamber is partially filled with a suspension of cells in an appropriate growth medium.

The specific procedures used to isolate the P1532 isolate are described in detail in Example 1. Briefly, an aliquot of soil suspension was placed in a diffusion chamber (similar to those described in U.S. Pat. No. 7,011,957) and the diffusion chamber was incubated on top of the soil from which the soil suspension in the chamber was obtained. After about 28 days of incubation at 25° C., the surface membrane of the diffusion chamber was peeled away and the chamber contents were transferred to a sterile Petri dish. Visible colonies were streaked on 2% SMS agar (2% SMS agar comprised of casein, 0.125 g; potato starch 0.1 g; casamino acids, 1 g; bacto agar, 20 g; distilled water, 1 L) plates and grown for about 1 to 3 weeks. Single colonies were picked and restreaked onto 2% SMS agar plates, and onto media richer in nutrients (2% SMS agar supplemented with 1.56 gram of LB broth base (Difco 241410) per liter). Single colonies are restreaked onto fresh plates until identified to be pure by visual examination under a dissecting microscope. Determination of purity is determined by morphological observations of shape, texture and color. Once pure, the isolates were used for further studies. P1532 was one of these colonies. Colonies of P1532 after 2 weeks of growth at about 25° C. on 2% SMS plates are filamentous colonies tightly embed in agar with a reddish orange center and white substrate mycelial edges. The rDNA analysis of the P1532 isolate indicated that the top blast hit on Genbank was 99.6% identical to a *Streptosporangium* species (Genbank® Accession No. AY996845; GI #62866418). Of course, any other method known to one of skill in the art may also be used to isolate the microorganism from an environment of interest.

In certain embodiments, a process for the production of NOVO3 comprises cultivating a P1532 isolate (ATCC Deposit No. PTA-8676) in a culture medium comprising assimilable sources of carbon, nitrogen, and inorganic salts under aerobic conditions to produce an assayable amount of NOVO3. Fermentation of P1532 to produce NOVO3 can be performed by any method known in the art. A non-limiting fermentation procedure for P1532 is described in Example 1. Briefly, the P1532 isolate is inoculated into a 250 ml Erlenmeyer flask in 40 ml of a seed medium (1.5% glucose, 1.5% glycerol, 1% malt extract, 0.5% casamino acids, 0.25% yeast extract and 0.05% calcium chloride dehydrate) and grown for 4 days at 28° C. and 200 rpm. The resulting cells are homogenized in a tissue blender and 5 ml of this solution inoculated into a 2 L Erlenmeyer flask containing 500 ml of a medium comprised of: 2% glucose, 2% glycerol, 1% soy flour, 1% cotton seed embryo, 0.1% ammonium sulfate, and 1% calcium carbonate or a medium consisting of 6% molasses, 2% soluble starch, 2% fish powder, 0.2% $CaCO_3$, 0.01% $CuSO_4$-$5H_2O$, 0.00005% NaI or a medium consisting of 3% molasses, 1% glycerol, 0.8% yeast extract, 0.4% peptone, 0.1% $CaCO_3$ or a medium consisting of 2% mannitol, 2% soybean flour, 0.02% $KH_2PO_4$, 0.005% $MgSO_4$-$7H_2O$, 0.1% minor salts solution ($FeSO_4$, $MnSO_4$, $ZnSO_4$-$7H_2O$, Borax, $CoCl_2$-$6H_2O$, $CuSO_4$-$5H_2O$, $Na_2MoO_4$-$2H_2O$) or a medium consisting of 1% glucose, 0.1% yeast extract, 0.01% casamino acids, 0.3% L-proline, 1% $MgCl_2$-$6H_2O$, 0.4% $CaCl_2$, 0.02% $K_2SO_4$, 0.56% TES, 0.1% minor salts solution ($FeSO_4$, $MnSO_4$, $ZnSO_4$-$7H_2O$, Borax, $CoCl_2$-$6H_2O$, $CuSO_4$-$5H_2O$, $Na_2MoO_4$-$2H_2O$) or a medium consisting of 1.2% wheat flour, 0.6% corn meal, 1% glucose, 0.5% yeast extract or a medium consisting of 1% pharmamedium, 1% malt extract, 0.2% $CaSO_4$, 0.5% casein, 0.1% minor salts solution, 1% fish oil or a medium consisting of 1% glucose, 1% glycerol, 0.5% oatmeal, 1% soybean flour, 0.5% yeast extract, 0.5% casamino acids, 0.1% CaCO$_3$. The resulting fermentation is then grown aerobically for at least 6 days at 28° C. and 200 rpm. NOVO3 is produced in the fermentation broth.

The isolation of NOVO3 from the fermentation broth can be achieved by any means known in the art, such as the methods described in Example 1. NOVO3 can be purified by any method known in the art including, but not limited to, normal phase chromatography, reverse phase chromatrgraphy, countercurrent chromatography, ion exchange chromatography, supercritical fluid chromatography or size exclusion chromatography.

The isolated NOVO3 can then be purified by any method known in the art including, but not limited to, high performance liquid chromatography, normal phase chromatography, reverse phase chromatrgraphy, countercurrent chromatography, ion exchange chromatography, supercritical fluid chromatography or size exclusion chromatography.

The isolated NOVO3 can be used as is or modified chemically. In certain embodiments, a compound of formula II can be prepared from a compound of formula I through a hydrogenation process (e.g., H$_2$ in the presence of a Pd catalyst) see, e.g., King, et al. *Handbook of Organopalladium Chemistry for Organic Synthesis* (2002), 2:2719-2752).

Similarly, a compound of formula IIa can be prepared from a compound of formula Ib by hydrogenation. Further chemical modifications can be carried out by one of ordinary skill in the art.

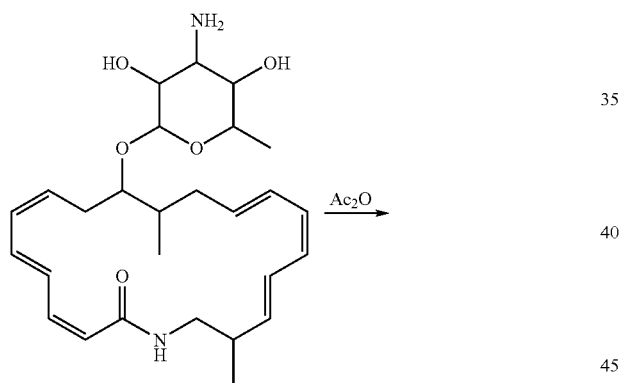

As shown directly above, NOVO3 may react at room temperature with acetic anhydride under a protective gas atmosphere to form the N-acetylated NOVO3 derivative.

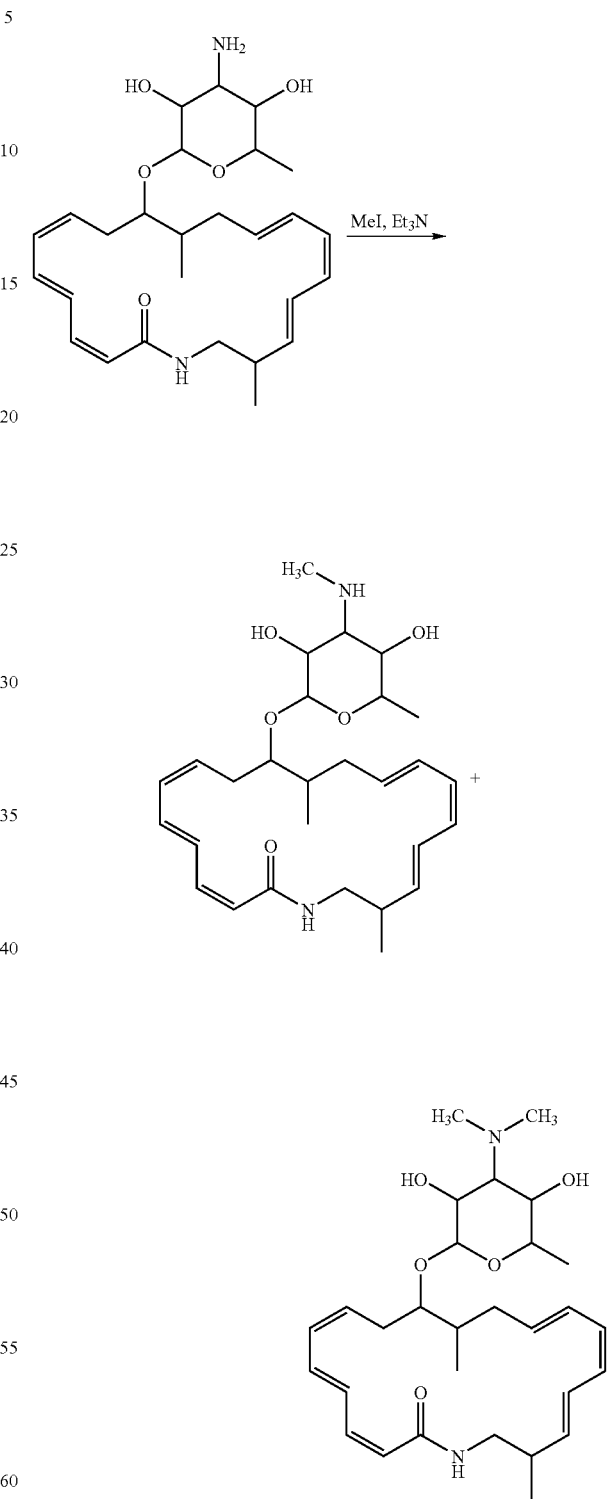

As shown directly above, NOVO3 may react at room temperature with iodomethane in the presence of triethylamine under a protective gas atmosphere to form the mono- and di-methylated NOVO3 derivatives, which can be separated by usual chromatographic methods.

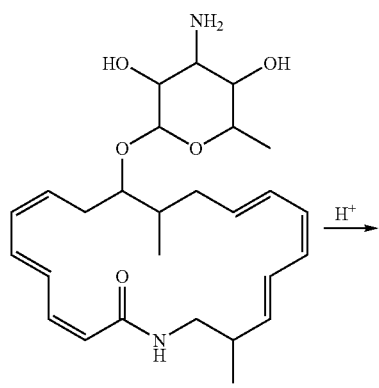

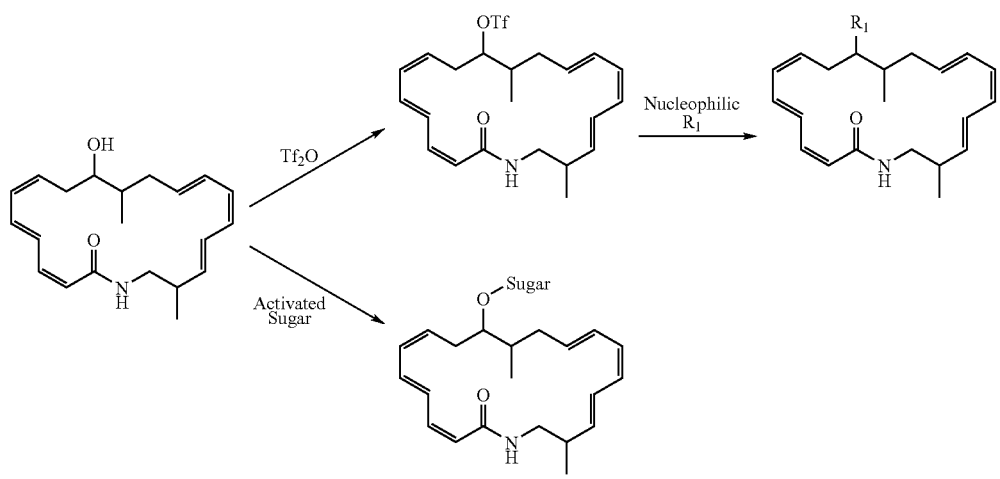

As shown directly above, NOVO3 may react with an acid to give the aglycone. Other sugar groups may then be introduced using appropriately activated sugar donors to form other corresponding glycosylated NOVO3 derivatives. Alternatively, the aglycone may be reacted with triflate anhydride under a protective gas atmosphere to form triflated aglycone. Reagents with nucleophilic $R_1$ may then be introduced at the position indicated.

-continued

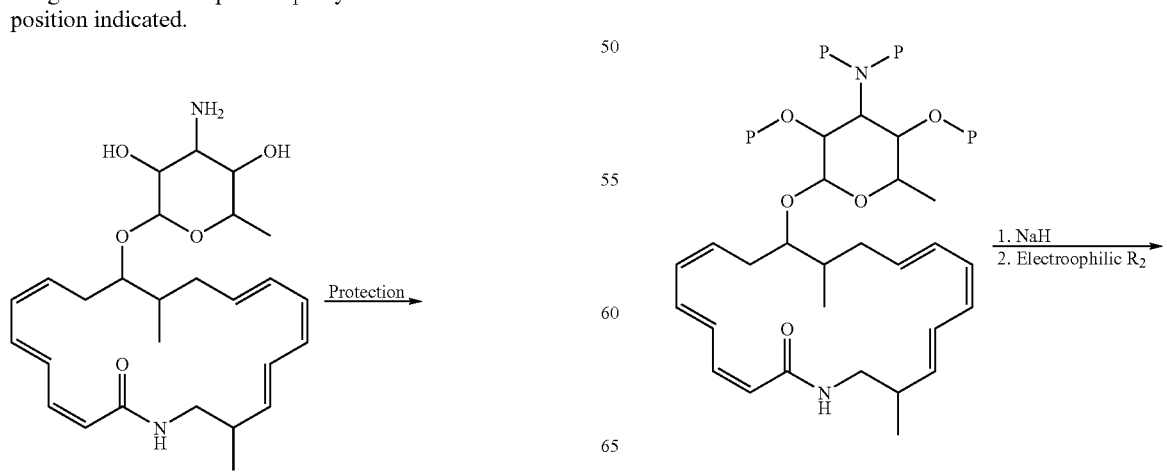

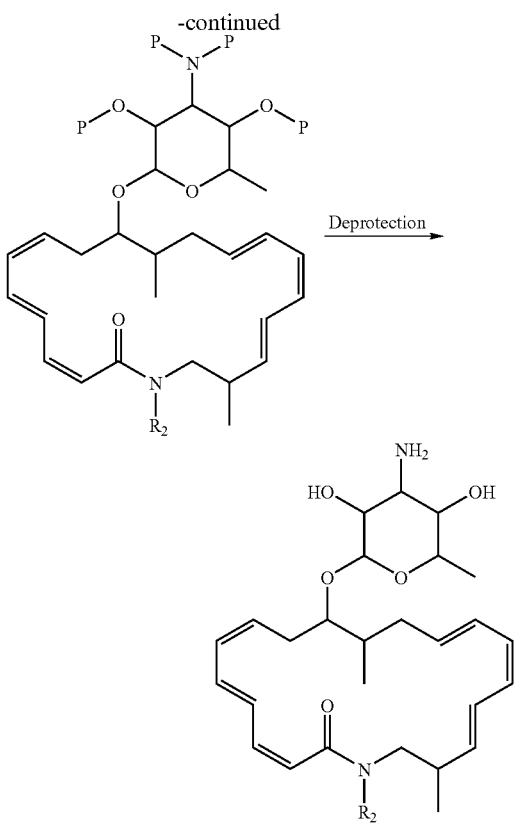

As depicted above, NOVO3 can be protected with appropriate protecting groups, followed by deprotonation of the amide using sodium hydride at low temperature. The $R_2$ group may then be introduced using appropriate reagents with electrophilic $R_2$. The protecting groups on the sugar moiety can then be removed to give the $R_2$ modified NOVO3 derivatives.

Methods of Treatment

In some aspects, the invention relates to methods of inhibiting the growth of a pathogen. The method involves contacting the pathogen with an effective amount of one or more macrolactam compounds of the invention thereby inhibiting the growth of the pathogen compared with the growth of the pathogen in the absence of treatment with a compound of the invention. In certain embodiments, the method reduces the growth of the pathogen compared with the growth of the pathogen in the absence of treatment with a compound of the invention. In other instances, the treatment results in the killing of the pathogen. Non-limiting examples of a pathogen include, but are not limited to, a bacterium, a fungus, a virus, a protozoan, a helminth, a parasite, and combinations thereof. These methods may be practiced in vivo, ex vivo, or in vitro.

The anti-bacterial activity of the macrolactam compounds of the invention with respect to a specific bacterium can be assessed by in vitro assays such as monitoring the zone of inhibition (Example 3) and the minimal inhibitory concentration (MIC) assays described in detail in Example 5.

The anti-fungal activity of the macrolactam compounds of the invention can be determined, for example, by following the viability of the desired fungal pathogens (such as *Candida albicans*, and *Aspergillus* species) for example as described in Sanati et al., A new triazole, voriconazole (UK-109,496), blocks sterol biosynthesis in *Candida albicans* and *Candida krusei*, *Antimicrob. Agents Chemother.*, 1997 November; 41(11): 2492-2496. Anti-viral properties of the macrolactam compounds of the invention can be determined, for example, by monitoring the inhibition of influenzae neuraminidase or by assaying viral viability as described in Tisdale M., Monitoring of viral susceptibility: new challenges with the development of influenza NA inhibitors, *Rev. Med. Virol.*, 2000 January-February; 10(1):45-55. Anti-protozoan activity of the macrolactam compounds of the invention can be determined by following the viability of protozoan parasites such as *Trichomonas vaginalis* and *Giardia lamblia* as described in Katiyar et al., Antiprotozoal activities of benzimidazoles and correlations with beta-tubulin sequence, *Antimicrob. Agents Chemother.*, 1994 September; 38(9): 2086-2090. Anthelminthic activity of the macrolactam compounds of the invention can be determined, for example, by following the effect of the compounds on the viability of nematodes such as *Schistosoma mansoni*, *Schistosoma cercariae* and *Caenorhabditis elegans* as described in Molgaard P. et al., Traditional herbal remedies used for the treatment of urinary schistosomiasis in Zimbabwe, *J. Ethnopharmacol.*, 1994 April; 42(2):125-32.

In other aspects, the invention is directed to methods of treating a disorder in a subject in need thereof, comprising administering to the subject an effective amount of one or more macrolactam compounds described herein. In certain embodiments, the disorder is caused by a pathogen such as, but not limited to, a bacterium, a fungus, a virus, a protozoan, a helminth, a parasite, or a combination thereof.

In some embodiments, the disorder is caused by a bacterium. The macrolactam compounds described herein can be useful against both Gram-positive and Gram-negative bacteria. Non-limiting examples of Gram-positive bacteria include *Streptococcus*, *Staphylococcus*, *Enterococcus*, *Corynebacteria*, *Listeria*, *Bacillus*, *Erysipelothrix*, and *Actinomycetes*. In some embodiments, the methods of the invention are used to treat an infection by one or more of: *Helicobacter pylori*, *Legionella pneumophilia*, *Mycobacterium tuberculosis*, *Mycobacterium avium*, *Mycobacterium intracellulare*, *Mycobacterium kansaii*, *Mycobacterium gordonae*, *Mycobacteria sporozoites*, *Staphylococcus aureus*, *Staphylococcus epidermidis*, *Neisseria gonorrhoeae*, *Neisseria meningitidis*, *Listeria monocytogenes*, *Streptococcus pyogenes* (Group A *Streptococcus*), *Streptococcus agalactiae* pyogenes (Group B *Streptococcus*), *Streptococcus dysgalactia*, *Streptococcus faecalis*, *Streptococcus bovis*, *Streptococcus pneumoniae*, pathogenic *Campylobacter* sporozoites, *Enterococcus* sporozoites, *Haemophilus influenzae*, *Pseudomonas aeruginosa*, *Bacillus anthracis*, *Bacillus subtilis*, *Escherichia coli*, *Corynebacterium diphtheriae*, *Corynebacterium jeikeium*, *Corynebacterium* sporozoites, *Erysipelothrix rhusiopathiae*, *Clostridium perfringens*, *Clostridium tetani*, *Clostridium difficile*, *Enterobacter aerogenes*, *Klebsiella pneumoniae*, *Pasturella multocida*, *Bacteroides thetaiotamicron*, *Bacteroides uniformis*, *Bacteroides vulgatus*, *Fusobacterium nucleatum*, *Streptobacillus moniliformis*, *Leptospira*, and *Actinomyces israelli*. In specific embodiments, the compounds described herein are useful in treating an infection by Methicillin Resistant *Staphylococcus aureus* (MRSA) or by Vancomycin Resistant Entercocci (VRE). MRSA contributes to approximately 19,000 deaths annually in the United States and although most of these deaths are due to hospital-acquired MRSA (HA-MRSA), it is the community-acquired MRSA (CA-MRSA) that is actually more virulent, and known to kill previously healthy individuals. The virulence of the CA-MRSA is in part due to the expression of phenol soluble modulins or PSM peptides. Accordingly, in treating CA-MRSA, one can use a compound of the invention in combination with an agent that modulates the expression and/or activity of virulence factors, such as, but not limited to, PSM peptides. In certain embodiments, the macrolactam compounds of the invention may be used to treat spirochetes such as *Borelia burgdorferi*, *Treponema pallidium*, and *Treponema pertenue*.

In other embodiments, the macrolactam compounds described herein may be useful in treating viral disorders. Non-limiting examples of infectious viruses that may be treated by the methods of the invention include: Retroviridae (e.g., human immunodeficiency viruses, such as HIV-1 (also referred to as HTLV-III, LAV or HTLV-III/LAV), or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses, severe acute respiratory syndrome (SARS) virus); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (e.g, Hepatitis B virus); Parvoviridae (parvoviruses); Papovaviridae (papilloma viruses, polyoma viruses); Adenoviridae (most adenoviruses); Herpesviridae (e.g., herpes simplex virus (HSV) 1 and 2, varicella zoster virus, cytomegalovirus (CMV), herpes viruses); Poxyiridae (e.g., variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). In specific embodiments, the compounds of the invention are used to treat a influenza virus, human immunodeficiency virus, and herpes simplex virus.

In some embodiments, the macrolactam compounds of the invention may be useful to treat disorders caused by fungi. Non-limiting examples of fungi that may be inhibited by the compounds of the invention include, but are not limited to, *Cryptococcus neoformans*, *Histoplasma capsulatum*, *Coccidioides immitis*, *Blastomyces dermatitidis*, *Chlamydia trachomatis*, *Candida albicans*, *Candida tropicalis*, *Candida glabrata*, *Candida krusei*, *Candida parapsilosis*, *Candida dubliniensis*, *Candida lusitaniae*, *Epidermophyton floccosum*, *Microsporum audouinii*, *Microsporum canis*, *Microsporum canis* var. *distortum* *Microsporum cookei*, *Microsporum equinum*, *Microsporum ferrugineum*, *Microsporum fulvum*, *Microsporum gallinae*, *Microsporum gypseum*, *Microsporum nanum*, *Microsporum persicolor*, *Trichophyton ajelloi*, *Trichophyton concentricum*, *Trichophyton equinum*, *Trichophyton flavescens*, *Trichophyton gloriae*, *Trichophyton megnini*, *Trichophyton mentagrophytes* var. *erinacei*, *Trichophyton mentagrophytes* var. *interdigitale*, *Trichophyton phaseoliforme*, *Trichophyton rubrum*, *Trichophyton rubrum* downy strain, *Trichophyton rubrum* granular strain, *Trichophyton schoenleinii*, *Trichophyton simii*, *Trichophyton soudanense*, *Trichophyton terrestre*, *Trichophyton tonsurans*, *Trichophyton vanbreuseghemii*, *Trichophyton verrucosum*, *Trichophyton violaceum*, *Trichophyton yaoundei*, *Aspergillus fumigatus*, *Aspergillus flavus*, and *Aspergillus clavatus*.

In yet other embodiments, the macrolactam compounds described herein may be useful in treating disorders caused by protozoans. Non-limiting examples of protozoa that can be inhibited by the compounds of the invention include, but are not limited to, *Trichomonas vaginalis*, *Giardia lamblia*, *Entamoeba histolytica*, *Balantidium coli*, *Cryptosporidium parvum* and *Isospora belli*, *Trypansoma cruzi*, *Trypanosoma gambiense*, *Leishmania donovani*, and *Naegleria fowleri*.

In certain embodiments, the macrolactam compounds described herein may be useful in treating disorders caused by helminths. Non-limiting examples of helminths that can be inhibited by the compounds of the invention include, but are not limited to: *Schistosoma mansoni*, *Schistosoma cercariae*, *Schistosoma japonicum*, *Schistosoma mekongi*, *Schistosoma hematobium*, *Ascaris lumbricoides*, *Strongyloides stercoralis*, *Echinococcus granulosus*, *Fasciolopis buski*, *Capillaria philippinensis*, *Paragonimus westermani*, *Ancylostoma dudodenale*, *Necator americanus*, *Trichinella spiralis*, *Wuchereria bancrofti*, *Brugia malayi*, and *Brugia timori*, *Toxocara canis*, *Toxocara cati*, *Toxocara vitulorum*, *Caenorhabiditis elegans*, and *Anisakis* species.

In some embodiments, the macrolactam compounds described herein may be useful in treating disorders caused by parasites. Non-limiting examples of parasites that can be inhibited by the compounds of the invention include, but are not limited to, *Plasmodium falciparum*, *Plasmodium yoelli*, *Hymenolepis nana*, *Clonorchis sinensis*, *Loa loa*, *Paragonimus westermani*, *Fasciola hepatica*, and *Toxoplasma gondii*. In specific embodiments, the parasite is a malarial parasite.

The macrolactam compounds of the invention are also envisioned for use in treating other disorders such as, but not limited to: cardiovascular disease, endocarditis, atherosclerosis, stroke, infections of the skin including burn wounds and skin infections in diabetics (e.g., diabetic foot ulcers), ear infections, upper respiratory tract infections, ulcers, nosocomial pneumonia, community-acquired pneumonia, sexually transmitted diseases, urinary tract infections, septicemia, toxic shock syndrome, tetanus, infections of the bones and joints, Lyme disease, treatment of subjects exposed to anthrax spores, hypercholesterolemia, inflammatory disorders, aging-related diseases, channelopathies, autoimmune diseases, graft-versus-host diseases and cancer.

In a specific embodiment, the macrolactam compounds of the invention are used to treat an inflammatory disease. Examples of inflammatory diseases include, but are not limited to: arthritis, osteoarthritis, rheumatoid arthritis, asthma, inflammatory bowel disease, inflammatory skin disorders, multiple sclerosis, osteoporosis, tendonitis, allergic disorders, inflammation in response to an insult to the host, sepsis, and systematic lupus erythematosus. Anti-inflammatory activity of the compounds of the invention can be assessed, for example, by measuring the ligand binding ability of the compounds to the formylpeptide receptor (FPR) family of G protein-coupled receptors (see, Young S. M. et al., High-throughput screening with HyperCyt flow cytometry to detect small molecule formylpeptide receptor ligands, *J Biomol Screen.*, 2005 June; 10(4):374-82) or by measuring the effect of such compounds on the secretion of pro-inflammatory cytokines in THP-1 cells after lipopolysaccharide stimulation (Singh et al., Development of an in vitro screening assay to test the anti-inflammatory properties of dietary supplements and pharmacologic agents, *Clin. Chem.*, 2005 December; 51(12):2252-6.). In certain embodiments, the macrolactam compounds of the invention inhibit metalloenzymes such as collagenases that destroy connective tissue and joint cartilage causing inflamed joints. In one embodiment, the macrolactam compounds of the invention are used to treat rheumatoid arthritis. In some embodiments the macrolactam compounds are administered in combination (either prior to, at the same time as, or after) with minocycline.

In another specific embodiment, the macrolactam compounds of the invention are used to treat a channelopathy. Channelopathies are diseases caused by disturbed function of ion channel subunits or the proteins that regulate them. Non-limiting examples of channelopathies include, but are not limited to, Alternating hemiplegia of childhood, Bartter syndrome, Brugada syndrome, Congenital hyperinsulinism, Cystic fibrosis, Episodic Ataxia, Erythromelalgia, Generalized epilepsy with febrile seizures plus, Hyperkalemic periodic paralysis, Hypokalemic periodic paralysis, Long QT syndrome, Malignant hyperthermia, Migraine, Myasthenia Gravis, Myotonia congenita, Neuromyotonia, Nonsyndromic deafness, Paramyotonia congenita, Periodic paralysis, Retinitis pigmentosa, Romano-Ward syndrome, Short QT syndrome, and Timothy syndrome. The effect of the compounds of the invention on channelopathies can be assayed, for example, via in vitro assays that utilize the desired ion channel, e.g., cystic fibrosis (CF) transmembrane conductance regulator (see, Fulmer S. B. et al., Two cystic fibrosis transmembrane conductance regulator mutations have different effects on both pulmonary phenotype and regulation of outwardly rectified chloride currents, *Proc. Natl. Acad. Sci. USA.,* 1995 Jul. 18; 92(15):6832-6).

In yet another specific embodiment, the macrolactam compounds of the invention are used to treat an aging-related disease. Non-limiting examples of aging-related diseases include, but are not limited to, Alzheimer's disease, and Parkinson's disease. The ability of the compounds of the invention to treat aging-related diseases can be tested, for example, by assays that monitor the compounds' activity on sirtuins, the NAD(+)-dependent histone/protein deacetylases (see, Borra M. T., Substrate specificity and kinetic mechanism of the Sir2 family of NAD+-dependent histone/protein deacetylases, *Biochemistry,* 2004 Aug. 3; 43(30):9877-87).

In some embodiments, the macrolactam compounds of the invention are used to treat an autoimmune disease. Non-limiting examples of autoimmune diseases include, but are not limited to, Acute disseminated encephalomyelitis, Addison's disease, Ankylosing spondylitis, Antiphospholipid antibody syndrome, aplastic anemia, Autoimmune hepatitis, Autoimmune Oophoritis, Celiac disease, Crohn's disease, Diabetes mellitus type 1, Gestational pemphigoid, Goodpasture's syndrome, Graves' disease, Guillain-Barré syndrome, Hashimoto's disease, Idiopathic thrombocytopenic purpura, Kawasaki's Disease, Lupus erythematosus, Multiple sclerosis, Myasthenia gravis, Opsoclonus myoclonus syndrome (OMS), Optic neuritis, Ord's thyroiditis, Pemphigus, Pernicious anaemia, Primary biliary cirrhosis, Rheumatoid arthritis, Reiter's syndrome, Sjögren's syndrome, Takayasu's arteritis, Temporal arteritis, Warm autoimmune hemolytic anemia, and Wegener's granulomatosis. The immunosuppressive properties of the compounds of the invention can be measured, for example, by utilizing the mixed lymphocyte reaction assay (see, Itoh T. et al., A modified method of mixed lymphocyte reaction: establishment of the assay system and its application to extracts of fungal cultures, *J. Antibiot.* (Tokyo), 1993 October; 46(10):1575-81).

In some embodiments, the macrolactam compounds of the invention are used to treat a cancer. In specific embodiments, the compounds are used to inhibit the growth of a cancer or tumor cell. In other specific embodiments, the compounds are used to kill the cancer or tumor cell. Examples of cancers include, but are not limited to, breast cancer, ovarian cancer, colon cancer, prostate cancer, liver cancer, lung cancer, gastric cancer, esophageal cancer, urinary bladder cancer, melanoma, leukemia, and lymphoma. The compounds of the invention may be administered with a chemotherapeutic agent. Non-limiting examples of chemotherapeutic agents include antimetabolites, purine or pyrimidine analogs, alkylating agents, crosslinking agents, and intercalating agent. The chemotherapeutic agent can be administered before, after, or substantially simultaneously with a compound of the invention. Anti-cancer activity of the compounds of the invention can be determined using, for example, cytotoxicity assays comparing the cytotoxicity of the compound of interest against cancer cells and normal (non-cancerous) mammalian cells (see, Roomi M. W. et al., In vivo and in vitro antitumor effect of ascorbic acid, lysine, proline, arginine, and green tea extract on human fibrosarcoma cells HT-1080, *Med. Oncol.,* 2006; 23(1):105-11) or by measuring angiogenic properties (see, Ivanov V. et al., Anti-angiogenic effects of a nutrient mixture on human umbilical vein endothelial cells, *Oncol. Rep.,* 2005 December; 14(6):1399-404).

In certain embodiments, the macrolactam compounds of the invention are administered to treat hypercholesterolemia. In specific embodiments, the compounds of the invention are administered to a subject to reduce the levels of low density lipoprotein (LDL) compared with the levels of LDL prior to administration of the compound to the subject. In another specific embodiment, the compounds of the invention are administered to a subject to increase the levels of high density lipoprotein (HDL) compared with the levels of HDL prior to administration of the compound to the subject. Cholesterol lowering activities of the compounds of the invention can be assayed, for example, by determining the ability of the compound of interest to inhibit 3-hydroxy-3-methylglutaryl-coenzyme A reductase (HMGCR), and/or on other enzymes involved in the mevalonate pathway downstream of HMGCR (see, Gerber R. et al., Cell-based screen of HMG-CoA reductase inhibitors and expression regulators using LC-MS, *Anal. Biochem.,* 2004 Jun. 1; 329(1):28-34). Macrolactam compounds of the invention can also be assessed for their potential to increase high density lipoprotein ("good" cholesterol) by measuring their ability to up-regulate scavenger receptor class B type I (SR-BI), the high-affinity high-density lipoprotein (HDL) receptor (see, Yang Y. et al., Identification of novel human high-density lipoprotein receptor Up-regulators using a cell-based high-throughput screening assay, *Biomol. Screen.,* 2007 March; 12(2):211-9).

In another embodiment, the macrolactam compounds of the invention are used to treat a cardiovascular disease. In specific embodiments, the macrolactam compounds of the invention are used to treat *Chlamydia pneumoniae* infection that results in complications of atherosclerosis, cardiovascular disease, and stroke. In one embodiment, the macrolactam compounds of the invention are used to treat endocarditis.

In certain embodiments, the macrolactam compounds of the invention are used as adjunct therapy for the treatment of the disorders described above.

In other embodiments, the macrolactam compounds of the invention are used to inhibit the growth of an infective agent compared with the growth of the infective agent in the absence of being treated by a compound of the invention. Non-limiting examples of infective agents include, but are not limited to, bacteria, fungi, viruses, protozoa, helminths, parasites, and combinations thereof. The macrolactam compounds may be used to inhibit the agent in vivo or in vitro.

Formulation

The invention also provides a pharmaceutical composition comprising at least one of the macrolactam compounds of the invention (or an enantiomer, diastereomer, tautomer, or pharmaceutically-acceptable salt or solvate thereof), and a pharmaceutically-acceptable carrier. These macrolactam compositions are suitable for administration to a subject (e.g., a mammal such as a human). The pharmaceutical composition can be used for treating a disorder. Non-limiting examples of disorders are provided above.

In one embodiment, the macrolactam compounds are administered in a pharmaceutically-acceptable carrier. Any suitable carrier known in the art may be used. Carriers that efficiently solubilize the agents are preferred. Carriers include, but are not limited to, a solid, liquid, or a mixture of a solid and a liquid. The carriers may take the form of capsules, tablets, pills, powders, lozenges, suspensions, emulsions, or syrups. The carriers may include substances that act as flavoring agents, lubricants, solubilizers, suspending agents, binders, stabilizers, tablet disintegrating agents, and encapsulating materials. The phrase "pharmaceutically-acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Non-limiting examples of materials which can serve as pharmaceutically-acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline, (18) Ringer's solution, (19) ethyl alcohol; (20) phosphate buffer solutions; and (21) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single-dosage form will vary depending upon the subject being treated, the particular mode of administration, the particular condition being treated, among others. The amount of active ingredient that can be combined with a carrier material to produce a single-dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the invention with the carrier and, optionally, one or more accessory ingredients. In general, the formulations are prepared by uniformly and intimately bringing into association a macrolactam compound of the present invention with liquid carriers, or timely divided solid carriers, or both, and then, if necessary, shaping the product.

In solid dosage forms of the invention for oral administration (e.g., capsules, tablets, pills, dragees, powders, granules, and the like), the active ingredient is mixed with one or more additional ingredients, such as sodium citrate or dicalcium phosphate, and/or any of the following: fillers or extenders, such as, but not limited to, starches, lactose, sucrose, glucose, mannitol, and/or silicic acid; binders, such as, but not limited to, carboxymethylcellulose, alginates, gelatin, polyvinyl pyrrolidone, sucrose, and/or acacia; humectants, such as, but not limited to, glycerol; disintegrating agents, such as, but not limited to, agar, calcium carbonate, potato or tapioca starch, alginic acid, certain silicates, and sodium carbonate; solution retarding agents, such as, but not limited to, paraffin; absorption accelerators, such as, but not limited to, quaternary ammonium compounds; wetting agents, such as, but not limited to, cetyl alcohol and glycerol monostearate; absorbents, such as, but not limited to, kaolin and bentonite clay; lubricants, such as, but not limited to, talc, calcium stearate, magnesium stearate, solid polyethylene glycols, sodium lauryl sulfate, and mixtures thereof, and coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

In powders, the carrier is a finely-divided solid, which is mixed with an effective amount of a finely-divided agent. Powders and sprays can contain, in addition to a compound of this invention, excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Tablets for systemic oral administration may include one or more excipients as known in the art, such as, for example, calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with one or more disintegrating agents (e.g., maize, starch, or alginic acid, binding agents, such as, for example, gelatin, collagen, or acacia), lubricating agents (e.g., magnesium stearate, stearic acid, or talc), inert diluents, preservatives, disintegrants (e.g., sodium starch glycolate), surface-active and/or dispersing agent. A tablet may be made by compression or molding, optionally with one or more accessory ingredients.

In solutions, suspensions, emulsions or syrups, an effective amount of the macro lactam compound is dissolved or suspended in a carrier, such as sterile water or an organic solvent, such as aqueous propylene glycol. Other compositions can be made by dispersing the agent in an aqueous starch or sodium carboxymethyl cellulose solution or a suitable oil known to the art. The liquid dosage forms may contain inert diluents commonly used in the art, such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Besides inert diluents, the oral compositions can also include adjuvants, such as wetting agents, emulsifying and suspending agents, sweetening, flavoring, coloring, perfuming, and preservative agents.

Suspensions, in addition to the active compound, may contain suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions for rectal or vaginal administration may be presented as a suppository, which may be prepared by mixing one or more compounds of the invention with one or more suitable non-irritating excipients or carriers comprising, for example, cocoa butter, polyethylene glycol, a suppository wax or a salicylate, and which is solid at room temperature but liquid at body temperature and, thus, will melt in the rectum or vaginal cavity and release the agents. Formulations suitable for vaginal administration also include pessaries, tampons, creams, gels, pastes, foams, or spray formulations containing such carriers as are known in the art to be appropriate.

Dosage forms for the topical or transdermal administration of a compound of this invention include powders, sprays, ointments, pastes, creams, lotions, gels, solutions, patches, and inhalants. The active macrolactam compound may be mixed under sterile conditions with a pharmaceutically-acceptable carrier, and with any preservatives, buffers, or propellants that may be required.

Ointments, pastes, creams, and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Trans dermal patches have the added advantage of providing controlled delivery of a compound of the present invention to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the macrolactam compound in a polymer matrix or gel.

The macrolactam compounds are administered in a therapeutic amount to a patient in need of such treatment. Such an amount is effective in treating a disorder of the patient. This amount may vary, depending on the activity of the agent utilized, the nature of the disorder, and the health of the patient. The term "therapeutically-effective amount" is used to denote treatments at dosages effective to achieve the therapeutic result sought. Furthermore, a skilled practitioner will appreciate that the therapeutically-effective amount of the macro lactam compound may be lowered or increased by fine-tuning and/or by administering more than one macrolactam compound, or by administering a macrolactam compound together with a second agent (e.g., antibiotics, antifungals, antivirals, NSAIDS, DMARDS, steroids, etc.). Therapeutically-effective amounts may be easily determined, for example, empirically by starting at relatively low amounts and by step-wise increments with concurrent evaluation of beneficial effect (e.g., reduction in symptoms). The actual effective amount will be established by dose/response assays using methods standard in the art (Johnson et al., *Diabetes*. 42:1179, (1993)). As is known to those in the art, the effective amount will depend on bioavailability, bioactivity, and biodegradability of the macrolactam compound.

A therapeutically-effective amount is an amount that is capable of reducing the symptoms of the disorder in a subject. Accordingly, the amount will vary with the subject being treated. Administration of the macrolactam compound may be hourly, daily, weekly, monthly, yearly, or a single event. For example, the effective amount of the macrolactam compound may comprise from about 1 µg/kg body weight to about 100 mg/kg body weight. In one embodiment, the effective amount of the compound comprises from about 1 µg/kg body weight to about 50 mg/kg body weight. In a further embodiment, the effective amount of the compound comprises from about 10 µg/kg body weight to about 10 mg/kg body weight. When one or more macrolactam compounds or agents are combined with a carrier, they may be present in an amount of about 1 weight percent to about 99 weight percent, the remainder being composed of the pharmaceutically-acceptable carrier.

The invention also provides for kits that comprise at least one macrolactam compound of the invention. The kits may contain at least one container and may also include instructions directing the use of these materials. In another embodiment, a kit may include an agent used to treat the disorder in question with or without such above-mentioned materials that may be present to determine if a subject has an inflammatory disease.

Administration of the Formulation

Methods of administration of the formulations of the invention comprising the macrolactam compounds of the invention described herein can be by any of a number of methods well known in the art. These methods include local or systemic administration. Exemplary routes of administration include oral, parenteral, transdermal, intradermal, intramuscular, intraperitoneal, intravenous, subcutaneous, intranasal (e.g., nebulizer, inhaler, aerosol dispenser), colorectal, rectal, intravaginal, and any combinations thereof. In addition, it may be desirable to introduce the pharmaceutical compositions of the invention into the central nervous system by any suitable route, including intraventricular and intrathecal injection. Intraventricular injection may be facilitated by an intraventricular catheter, for example, attached to a reservoir, such as an Ommaya reservoir. Methods of introduction may also be provided by rechargeable or biodegradable devices, e.g. depots. Furthermore, it is contemplated that administration may occur by coating a device, implant, stent, or prosthetic. The compounds of the invention can also be used to coat catheters in any situation where catheters are inserted in the body.

In another embodiment, the subject macrolactam compounds can be administered as part of a combinatorial therapy with other agents. Combination therapy refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously or sequentially. Thus, an individual who receives such treatment can have a combined (conjoint) effect of different therapeutic compounds.

For example, macrolactam compounds of the invention may be used in combination with other known antibiotics. The macrolactam compounds of the invention may either be administered sequentially or substantially at the same time. Varying the antibiotic can be helpful in reducing the ability of the pathogen to develop resistance to the drug. Non-limiting examples of antibiotics include penicillins (e.g., natural penicillins, penicillinase-resistant penicillins, antipseudomonal penicillins, aminopenicillins), tetracyclines, macrolides (e.g., erythromycin), lincosamides (e.g., clindamycin), streptogramins (e.g., Synercid), aminoglycosides, and sulfonamides. In some embodiments, the macrolactam compounds of the invention are used in combination with compounds that target virulence factors such as, but not limited to, phenol-soluble modulins. In some embodiments, the macrolactam compounds of the invention are used in combination with compounds that target the efflux pumps of the pathogens.

In other embodiments, for example, in the case of inflammatory conditions, the subject macrolactam compounds can be administered in combination with one or more other agents useful in the treatment of inflammatory diseases or conditions. Agents useful in the treatment of inflammatory diseases or conditions include, but are not limited to, anti-inflammatory agents, or antiphlogistics. Antiphlogistics include, for example, glucocorticoids, such as cortisone, hydrocortisone, prednisone, prednisolone, fluorcortolone, triamcinolone, methylprednisolone, prednylidene, paramethasone, dexamethasone, betamethasone, beclomethasone, fluprednylidene, desoxymethasone, fluocinolone, flunethasone, diflucortolone, clocortolone, clobetasol and fluocortin butyl ester; immunosuppressive agents such as anti-TNF agents (e.g., etanercept, infliximab) and IL-1 inhibitors; penicillamine; non-steroidal anti-inflammatory drugs (NSAIDs) which encompass anti-inflammatory, analgesic, and antipyretic drugs such as salicyclic acid, celecoxib, difunisal and from substituted phenylacetic acid salts or 2-phenylpropionic acid salts, such as alclofenac, ibutenac, ibuprofen, clindanac, fenclorac, ketoprofen, fenoprofen, indoprofen, fenclofenac, diclofenac, flurbiprofen, piprofen, naproxen, benoxaprofen, carprofen and cicloprofen; oxican derivatives, such as piroxican; anthranilic acid derivatives, such as mefenamic acid, flufenamic acid, tolfenamic acid and meclofenamic acid, anilino-substituted nicotinic acid derivatives, such as the fenamates miflumic acid, clonixin and flunixin; heteroarylacetic acids wherein heteroaryl is a 2-indol-3-yl or pyrrol-2-yl group, such as indomethacin, oxmetacin, intrazol, acemetazin, cinmetacin, zomepirac, tolmetin, colpirac and tiaprofenic acid; idenylacetic acid of the sulindac type; analgesically active heteroaryloxyacetic acids, such as benzadac; phenylbutazone; etodolac; nabunetone; and disease modifying antirheumatic drugs (DMARDs) such as methotrexate, gold salts, hydroxychloroquine, sulfasalazine, ciclosporin, azathioprine, and leflunomide. Other therapeutics useful in the treatment of inflammatory diseases or conditions include antioxidants. Antioxidants may be natural or synthetic. Antioxidants are, for example, superoxide dismutase (SOD), 21-aminosteroids/aminochromans, vitamin C or E, etc. Many other antioxidants are well known to those of skill in the art. The subject compounds may serve as part of a treatment regimen for an inflammatory condition, which may combine many different anti-inflammatory agents. For example, the macrolactam compounds may be administered in combination with one or more of an NSAID, DMARD, or immunosuppressant. In one embodiment of the application, the subject compounds may be administered in combination with methotrexate. In another embodiment, the subject antibodies may be administered in combination with a TNF-α inhibitor.

In the case of cardiovascular disease conditions, and particularly those arising from atherosclerotic plaques, which are thought to have a substantial inflammatory component, the subject compounds can be administered in combination with one or more other agents useful in the treatment of cardiovascular diseases. Agents useful in the treatment of cardiovascular diseases include, but are not limited to, β-blockers such as carvedilol, metoprolol, bucindolol, bisoprolol, atenolol, propranolol, nadolol, timolol, pindolol, and labetalol; antiplatelet agents such as aspirin and ticlopidine; inhibitors of angiotensin-converting enzyme (ACE) such as captopril, enalapril, lisinopril, benazopril, fosinopril, quinapril, ramipril, spirapril, and moexipril; and lipid-lowering agents such as mevastatin, lovastatin, simvastatin, pravastatin, fluvastatin, atorvastatin, and rosuvastatin.

In the case of cancer, the subject macrolactam compounds can be administered in combination with one or more anti-angiogenic factors, chemotherapeutics, or as an adjuvant to radiotherapy. It is further envisioned that the administration of the subject compounds will serve as part of a cancer treatment regimen, which may combine many different cancer therapeutic agents.

Reference will now be made to specific examples illustrating the invention. It is to be understood that the examples are provided to illustrate preferred embodiments and that no limitation to the scope of the invention is intended thereby.

EXAMPLES

Example 1

Isolation of NOVO3

An aliquot of soil collected from a fallow corn field in New York (labeled as SRC000135) was ground using a mortar and pestle. A volume of 10 ml of SMSS broth (casein, 0.125 g; potato starch, 0.5 g; casamino acids, 5 g; glycerol, 2 ml; yeast extract, 100 mg, distilled water, 998 ml; 0.16 µM magnesium sulphate, 0.420 nM calcium chloride, 1 µM potassium phosphate buffer, pH 7.0) was added for every gram of soil utilized. Antibiotics (50 µg/ml final concentration of cefotaxime, imipenem and tobramycin) were added to 10 ml of the soil suspension and incubated at room temperature with gentle shaking for 16 hr, after which, 1 ml of the soil suspension was mixed with 9 ml of sterile water. A 100 µl volume aliquot of this dilution was added to 3 ml of 1% SMS agar (casein, 0.125 g; potato starch, 0.5 g; casamino acids, 1 g; bacto-agar, 20 g; distilled water, 1 L) supplemented with anti-fungal agents (final concentration of cycloheximide being 100 µg/ml, and of nystatin being 50 µg/ml), and quickly poured into a diffusion chamber.

The diffusion chamber consisted of a steel washer sealed on one side with a 0.03 micron pore-sized polycarbonate membrane (see, U.S. Pat. No. 7,011,957). Once the agar solidified, the open face of the chamber was sealed with another 0.03 micron pore-sized polycarbonate membrane, and the chamber placed on top of moist SRC000135 soil so that there was good contact between the chamber contents and the soil. After 28 days incubation the surface membrane (facing away from the soil) was peeled off, and the chamber contents were transferred to a sterile Petri dish. Each visible colony was picked by stabbing colonies with a sterile 28 Gauge wire and streaked onto the surface of 2% SMS agar (10 ml of 2% SMS agar in sterile 10 cm Petri dish). Several colonies, including a light orange colony, were picked in this way. After 1 to 3 weeks growth on the agar surface, colonies were further purified (if needed) by streaking onto sterile 2% SMS agar dishes, and onto 2% SMS agar supplemented with 1.56 g of LB broth base (Difco 241410) per liter.

P1532, the producer of NOVO3, was one of these colonies directly picked from the diffusion chamber. Once the colonies of P1532 were shown to be pure by visual examination under a dissecting microscope, about $10^6$ growing cells were disrupted by vortexing in the presence of beads (acid washed glass beads, less than 106 µm), and 1 µl of the supernatant was used as a template for PCR. The 16S rDNA region was amplified using the universal primers Bac8F (5'-AGR GTT TGA TCC TGG CTC AG-3' (SEQ ID NO:1)), and 1492R (5'-TAC GGY TAC CTT GTT ACG ACT T-3' (SEQ ID NO:2)). The PCR product was sequenced successfully using primer 782R (5'-ACC AGG GTA TCT AAT CCT GT-3' (SEQ ID NO:3)). The top blast hit to the GenBank database was 99.6% to a Streptosporangium species (Accession # AY996845, GI #62866418). P1532 was deposited with the ATCC®, 10801 University Boulevard, Manassas, Va. 20110-2209, USA on Oct. 5, 2007, and assigned ATCC Patent Deposit Designation PTA-8676.

The fermentation procedure for P1532 was conducted as described below. P1532 was inoculated onto the surface of 2% SMS agar (casein, 0.125 g; potato starch 0.1 g; casamino acids, 1 g; bacto agar, 20 g; distilled water, 1 L) from a frozen permanent stock kept at −80° C. After 7 days of growth a colony was inoculated into 250 ml Erlenmeyer flasks containing 40 ml of a seed medium (glucose (1.5%), glycerol (1.5%), malt extract (1%), casamino acids (0.5%), yeast extract (0.25%) and calcium chloride $2H_2O$ (0.005%)). After growing the strain in this seed medium for 4 days at 28° C. and at 200 rpm, the resulting masses of orange cells were homogenized in a tissue blender. 5 ml of this cell solution was then inoculated into 500 ml in a 2000 ml baffled Erlenmeyer flask of a medium comprised of glucose (2%), glycerol (2%), soy flour (1%), cotton seed embryo (1%), ammonium sulfate (0.1%) and calcium carbonate (1%). Production of NOVO3 was achieved after 6 days of aerobic fermentation of P1532 at 28° C. and 200 rpm.

Two isolation procedures have been used to purify the NOVO3 compound from crude fermentation broth. Either of these procedure may be employed to isolate NOVO3.

The first NOVO3 isolation procedure is as follows: Crude fermentation broth was centrifuged at 18,000 g. The supernatant was passed over a plug of HP-20. NOVO3 was present only in the effluent. The effluent was then passed over a weak cation exchange resin. After NOVO3 was eluted with 5% ammonium hydroxide, the eluant was extracted with ethyl acetate (1:1) three times and the ethyl acetate portion, which contained NOVO3, was concentrated to dryness. The residue was reconstituted in DMSO and purified by HPLC on a C-18 column (Zorbax SB-C18 9.4×250 mm, 5 µm), eluting at 15.8 min. ($H_2O$/ACN with 0.1% TFA, 30-55% ACN over 30 min.). The sample was then lyophilized to dryness after the removal of acetonitrile.

The second NOVO3 isolation procedure is as follows: Crude fermentation broth was extracted with n-butanol (1:1). The emulsion was then centrifuged at 10,000 g, separating the aqueous layer from the organic layer containing NOVO3. The organic layer was then concentrated to dryness and the residue was dissolved in a minimal amount of $CHCl_3$:MeOH (1:1). The suspension was then added to 500 ml of ether:hexanes (3:2). The precipitate was isolated by centrifugation, dissolved in $CHCl_3$:MeOH (1:1), and dried onto HP-20 resin with periodic additions of water. The loaded HP-20 resin was added to a bed of fresh HP-20 resin and eluted with MeOH:$H_2O$ using a step gradient (0-100% MeOH). The majority of NOVO3 was present in the 80%, 90% and 100% elutions. These fractions were then concentrated to dryness and purified by HPLC on a C-18 column (Zorbax SB-C18 9.4×250 mm, 5 µm), eluting at 15.8 min. ($H_2O$/ACN with 0.1% TFA, 30-55% ACN over 30 min). The sample was then lyophilized to dryness after the removal of acetonitrile.

Example 2

Elucidation of the Structure of NOVO3

The structure of NOVO3 was elucidated using several NMR experiments, including GCOSY, GHSQC, and GHMBC. Multiple $^3J_{H-H}$ and $^1J_{C-H}$ were observed that allowed for the assignment of the macrolactam portion of NOVO3. Critical HMBC correlations confirmed the position of the sugar and aided in the assignment of the macrolactam backbone. The presence of the sugar moiety was first observed from in-source fragmentation in LC-MS experiments and later confirmed by NMR experiments. These data, in conjunction with high resolution mass measurements, MS-MS fractionation studies, and UV-VIS spectral analysis were utilized to solve the structure of NOVO3.

All NMR spectra were taken on a Bruker-DRX-500 spectrometer equipped with a 5 mm QNP probe. High resolution ESI-LC-MS data were recorded on a MicroMass Q-Tof-2 spectrometer equipped with an Agilent 1100 solvent delivery system and a DAD using a Phenomenex Gemini-C18 reversed phase column (50×2.0 mm, 3 µm particle size). Elution was performed with a linear gradient using deionized water with 0.1% formic acid and acetonitrile with 0.1% formic acid as solvents A and B, respectively, at a flow rate of 0.2 ml/min. The gradient increased from 10% to 100% of solvent B over 20 minutes followed by an isocratic elution at 100% of solvent B for 8 minutes.

The formula of NOVO3 was determined to be $C_{27}H_{40}N_2O_5$ based on the [MH]$^+$ adduct (calc. $[C_{27}H_{41}N_2O_5]^+$=473.3010, obs. $[C_{27}H_{41}N_2O_5]^+$=473.3040). See FIGS. 1 and 2 for $^1H$ and GCOSY spectra, respectively.

The structure of NOVO3 was confirmed by multiple HMBC correlations. Additionally, 10 mg of crude NOVO3 was dissolved in 0.5 mL of pyridine and 0.5 mL of acetic anhydride and allowed to react without agitation at RT overnight. The solution was evaporated to dryness and subsequently purified by HPLC. The assignment for the acetylated analog also appears in Table 1 below.

TABLE 1

$^1H$ and $^{13}C$ NMR (500 MHz) data for NOVO3 (δ in ppm)

| | NOVO3 (DMSO-$d_6$) | | NOVO3-Ac (DMSO-$d_6$) | |
|---|---|---|---|---|
| Position | d ($^{13}C$)$^a$ | d ($^1H$) | d ($^{13}C$)$^a$ | d ($^1H$) |
| 1 | 166.5 | | 166.3 | |
| 2 | 122.4 | 5.63 | 122.2 | 5.63 |
| 3 | 138.3 | 6.26 | 138.2 | 6.26 |
| 4 | 128.6 | 7.24 | 128.0 | 7.22 |
| 5 | 137.3 | 6.32 | 137.4 | 6.40 |
| 6 | 134.9 | 6.40 | 134.5 | 6.38 |
| 7 | 131.9 | 5.82 | 131.6 | 5.82 |
| 8 | 35.5 | 2.53 | 35.7 | 2.49 |
| | | 2.61 | | 2.60 |
| 9 | 84.0 | 3.41 | 84.3 | 3.38 |
| 10 | 38.3 | 1.23 | 37.7 | 1.27 |
| 10a | 16.6 | 0.94 | 16.3 | 0.95 |
| 11 | 34.5 | 1.56 | 35.0 | 1.56 |
| | | 2.19 | | 2.19 |
| 12 | 130.9 | 5.68 | 131.7 | 5.70 |
| 13 | 132.1 | 6.06 | 132.4 | 6.06 |
| 14 | 132.1 | 6.06 | 132.6 | 6.06 |
| 15 | 127.2 | 6.33 | 127.3 | 6.32 |
| 16 | 129.8 | 5.98 | 129.7 | 5.99 |
| 17 | 135.7 | 5.06 | 135.6 | 5.06 |
| 18 | 30.2 | 3.41 | 30.4 | 3.41 |
| 18a | 18.5 | 0.89 | 18.4 | 0.89 |
| 19 | 45.3 | 2.41 | 45.8 | 2.41 |
| | | 3.33 | | 3.33 |
| NH-1 | | 7.97 | | 7.98 |
| 1' | 101.8 | 4.80 | 99.56 | 4.77 |
| 2' | 66.2 | 3.70 | 67.6 | 4.69 |
| 2'-OH | | 5.56 | | |
| 3' | 47.5 | 3.37 | 44.3 | 4.43 |
| 3'-$NH_2$ | | 8.07 | | |
| 4' | 67.7 | 3.58 | 69.1 | 4.92 |
| 4'-OH | | 4.73 | | |
| 5' | 66.2 | 3.99 | 65.2 | 4.21 |
| 5'a | | 1.15 | 16.3 | 1.01 |
| 1-Ac | | | 170.2 | |

TABLE 1-continued

¹H and ¹³C NMR (500 MHz) data for NOVO3 (δ in ppm)

| Position | NOVO3 (DMSO-d₆) | | NOVO3-Ac (DMSO-d₆) | |
|---|---|---|---|---|
| | d (¹³C)ᵃ | d (¹H) | d (¹³C)ᵃ | d (¹H) |
| 2-Ac | | | 21.2 | 2.10 |
| NH-2 | | | | 7.70 |
| 1-Ac' | | | 169.4 | |
| 2-Ac" | | | 22.4 | 1.83 |
| 1-Ac" | | | 170.5 | |
| 2-Ac" | | | 21.0 | 2.12 |

ᵃAssignments were also confirmed by HSQC and HMBC correlations.

Example 3

NOVO3 has Antibacterial Activity

Antibacterial activity was demonstrated by measuring the ability of different concentration of NOVO3 to inhibit the growth of bacterial cells. This can be achieved in different assay format; bacteria growing on solid agar media or bacteria growing in broth such as for Example 5 and 6 (Minimal Inhibition Concentration).

For solid agar format, bacterial cells are first grown in a suitable media such as Mueller Hinton broth (MHB) until exponential phase ($OD_{600}$<1.0). The cells are diluted back to $OD_{600}$=0.02 in MHB, and evenly applied as a thin layer on the surface of a plate of solid growth media, such as MHB agar (about 0.1 ml onto a surface area of 100 cm²). After the surface is dried, a 5 µl aliquot of a 2-fold serial dilution of NOVO3 (in 50% DMSO) is spotted onto the surface of the agar plate. After 16 to 24 hr of incubation, depending on the bacterial strain of interest, the diameter of zones of growth inhibition are measured. For the purpose of demonstrating antibacterial activity of NOVO3, the results are presented as the minimal concentration of NOVO3 in which a 5 µL aliquot spotted onto a lawn of growing bacteria would result in a observable zone of no growth of the bacterial strain. The data in the table below demonstrates that NOVO3 has antibacterial activity.

TABLE 2

| Bacteria Strain | Growth Inhibition with 5 µl of NOVO3 |
|---|---|
| B. subtilis 1A1 | 0.125 µg/ml |
| B. anthracis Sterne | 1.25 µg/ml |
| MRSA NRS1 | 1.25 µg/ml |
| MRSA NRS108 | 1.25 µg/ml |
| E. faecalis ATCC 51575 (VRE) | 5 µg/ml |
| E. faecalis ATCC 51299 (VRE) | 1.25 µg/ml |
| E. faecalis BM4147 (VRE) | 1.25 µg/ml |

Example 4

Determination of NOVO3 Cytotoxicity

Mammalian cytotoxicity assays were performed using NIH3T3 mouse embryonic fibroblasts (ATCC CRL-1658), and cytotoxicity was measured using the CellTiter 96® AQueous One Solution Cell Proliferation Assay (Promega, Madison, Wis., Cat: G3582), according to the manufacturer's recommendations.

100× working stocks of 2-fold serial dilution of NOVO3 in DMSO were created in a 96 well format. The highest concentration of the 100× concentration (working stock) was prepared by adding 0.32 µl of the stock solution of NOVO3 (10 mg/ml in DMSO) for every 0.68 µl of DMSO to well A02. Then 0.5 µl of this 100× stock was added for every 0.5 µl of DMSO in well A03 and so on to create a total of 18 two-fold serial dilution series, from 3200 µg/ml to 0.025 µg/ml (from highest in well A02 to A10, then B02 to lowest in well B10). A control of DMSO was also included (wells in column A01, and A12). A second control consisting of the compound alone at the highest concentration (3200 µg/ml) was also set up in well A11.

An exponentially growing population of NIH/3T3 mouse embryonic fibroblast cells was trypsinized into single cell suspension and seeded at 3000 cells per 100 µl in all wells, except column 11 and 12 of a sterile 96-well flat bottom plate. After 24 hr at 37° C., 5% $CO_2$ in air, the supernatant was removed and replaced with 99 µl of growth media (Dulbecco's Modified Eagle's medium (ATCC®, Manassas, Va., Cat: 30-2002) supplemented with 10% calf bovine serum (ATCC® Cat: 30-2030)) that was pre-incubated at 37° C., 5% $CO_2$ in air, to all wells of the plate. A 1 µl aliquot of the 100× working stocks was added to the wells of the assay plate. The highest tested final concentration of NOVO3 was 32 µg/ml in well A02 and the lowest is 0.00025 µg/ml in well B10. DMSO (without compound) was added to the wells in column 1, and 12 such that well A01, and well B01 were cells only controls, and well A12, and well B12 were media only controls. The highest tested concentration of NOVO3 (32 µg/ml) was also added to the media only (no cell) control in well A11 to verify that compound alone does not contribute to the final measured signal. The plate was incubated at 37° C., 5% $CO_2$ in air for 24 hr.

Figure 3:
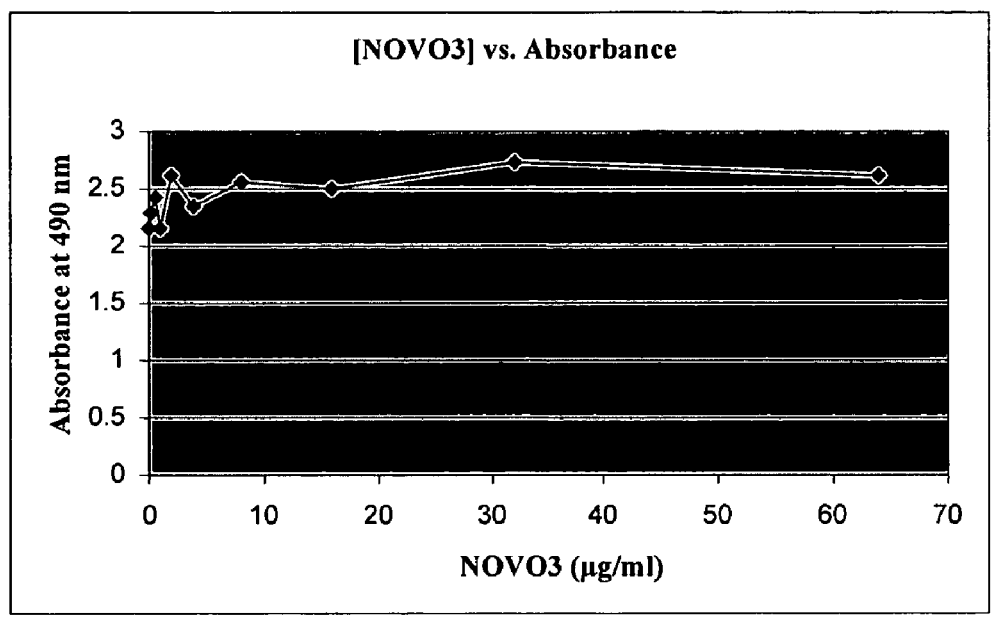
FIG. 3 is a graphic representation of absorbance at 490 nm of increasing concentrations of NOVO3 (μg/ml).

The plate was visually inspected under a dissecting microscope, and the absorbance at 490 nm was read using a Spectramax Plus Spectrophotometer, with wells A12, and B12 reserved as blanks (FIG. 3). The signal of compound alone (well A11) was verified not to contribute to the absorbance at this wavelength. Next, 20 µl of the CellTiter 96® AQueous One Solution Cell Proliferation Assay (Promega, Madison, Wis., Cat: G3582) was added to each well, and the plate was read after 3 hr of incubation. To calculate the effect of NOVO3 on mammalian cytotoxicity, the signal strengths from wells with NOVO3 were divided by the averaged signal from the controls containing cells only (well A01 and B01). The $LD_{50}$ was reported as the concentration of NOVO3 in which there is only 50% of the control signal.

The $LD_{50}$ of NOVO3 on NIH3T3 cells is >32 µg/ml, indicating that at the concentration where there is antibacterial activity, there is no observable toxicity on NIH3T3 cells measured by this assay.

The effect of NOVO3 on the hemolysis of human red blood cells was also tested. A total of 10 ml of expired packed red blood cells from the blood bank was gently added to 80 ml of PBS (Phosphate buffered saline), and pelleted at 1000 g for 5 minutes at 4° C. The upper phase and buffy layer (white blood cells) were removed. The cells are repeatedly washed by gentle mixing with PBS, and centrifugation until the upper phase is clear. In the last wash, 40 ml of 1×PBS with 0.05% BSA was added to half of the red blood cells while 40 ml of 1×PBS without BSA was added to the other half. The upper phase of the last wash was removed to leave a total volume of about 10 ml. The concentration of the red blood cells was measured by using the spectrophotometer at 600 nm. An aliquot of the cells are diluted to a final density $OD_{600}$ of 24 in 1×PBS, and another to a final density $OD_{600}$ of 24 in 1×PBS with 0.05% BSA.

The compound NOVO3 is two-fold serially diluted (similar to that described above for mammalian NIH3T3 cytotoxicity assay) as 100× concentration in DMSO, ranging from 12.5 µg/ml to 3200 µg/ml. A 1 µl aliquot of the 100× working stocks was added to the wells of the assay plate (U-bottom 96 well polystyrene plate) such that the highest concentration of 3200 µg/ml NOVO3 is in column 2 (eg., well position A2), and the lowest concentration of 12.5 µg/ml NOVO3 is in column 10. Control of 1 µl of DMSO is added to wells in column 1, 11, and 12. Aliquots (99 µl) of red blood cells in 1×PBS with and without 0.05% BSA are added. After incubation at 37° C. for 1 hour, the cells in the plates are pelleted by centrifugation at 1000 g for 5 minutes at 4° C. A 10 µl aliquot of the supernatant is removed from each well without disturbing the pellet, and transferred to clean plates containing 90 µl of 1×PBS per well. After thorough mixing, the absorbance at 450 nm was read using a Spectramax Plus Spectrophotometer, with wells A12, and B12 reserved using a Spectramax Plus Spectrophotometer, using wells with only 1×PBS as blanks.

Figure 4:
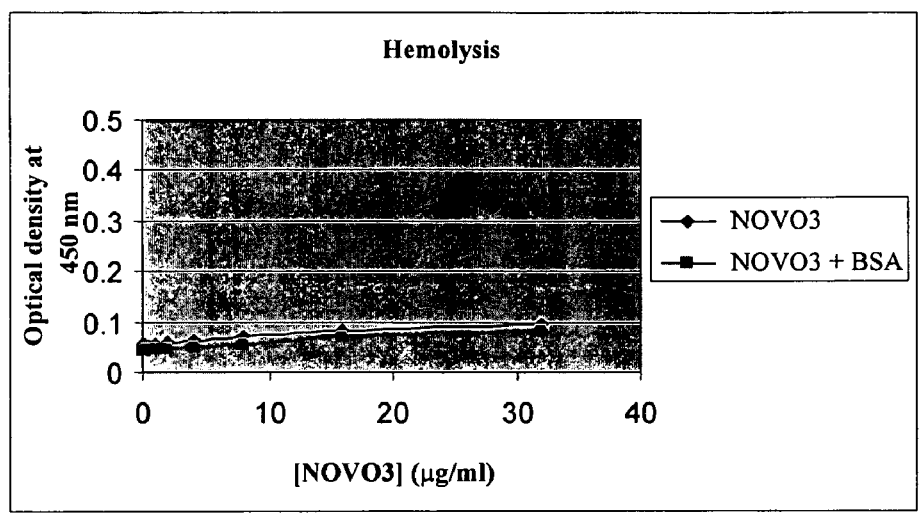
FIG. 4 is a graphic representation of the results of a hemolysis assay measuring the amount of hemoglobin release from red blood cells in the presence of increasing concentrations of NOVO3 by measuring the optical density 450 nm.

The absorbance at 450 nm measured the amount of hemoglobin released by the lysis of red blood cells (FIG. 4). A 0.025% of Triton X100 will result in complete lysis of red blood cells, and under these conditions give an absorbance of 0.41 at 450 nm. Even at the highest concentration of NOVO3 tested, whether in the presence or absence of 0.05% BSA, no significant hemolysis appeared.

Example 5

Determination of the Minimal Inhibitory Concentration of NOVO3

Bacterial cells such as MRSA (Methicillin-resistant *Staphylococcus aureus*) and VRE (Vancomycin resistant enterococci) were grown in a suitable media such as Mueller Hinton broth (MHB) until exponential phase ($OD_{600}<1.0$). 100× working stocks of 2-fold serial dilution of NOVO3 in DMSO is created in a 96 well format. The highest concentration of the 100× concentration (working stock) was prepared by adding 0.32 µl of the stock solution of NOVO3 (10 mg/ml in DMSO) for every 0.68 µl of DMSO to well A02. Then, 0.5 µl of this 100× stock was added for every 0.5 µl of DMSO in well A03 and so on, to create a total of 18 two-fold serial dilution series, from 3200 µg/ml to 0.025 µg/ml (from highest in well A02 to A10, then B02 to lowest in well B10). A control of just DMSO was also included (wells in column 1, and 12). A second control of compound alone at the highest concentration (3200 µg/ml) was also set up in well A11. The exponentially growing bacteria cells were diluted to $OD_{600}$ of 0.001, in the media appropriate for the test bacteria, such as Mueller Hinton broth for *Staphylococcus aureus*. Supplements can be added to the growth media such as Tween 80 (Fisher Cat T164), in order to reduce potential binding of the compound to plastic surfaces or with other supplements such as bovine serum albumin (Sigma A3059). A volume of 99 µl of this dilution was added to all wells of cell assay plates (U-bottom 96-well plate) except for columns 11 and 12 (which have 99 µl of media only). 1 µl of the 100× working stocks of NOVO3 was added to the cell assay plate. In this way, 1 µl of the 3200 µg/ml NOVO3 in well A02 when added to a final of 100 µl volume was equal to 32 µg/ml of NOVO3, while 1 µl of the next highest concentration when added to a final of 100 µl volume is equal to 16 µg compound per ml, and so on. Well A01, B01 only had cells but no NOVO3; well A11 has no cells but only 32 µg/ml NOVO3; while well A12, and B12 had only media but no cells, and no NOVO3. Controls such as vancomycin, erythromycin and kanamycin are handled similarly. The cell assay plates with compounds added were incubated at 37° C. and 20 hr for MRSA. After incubation, the plates were visually examined by a dissecting microscope, and then read using a Molecular Devices SpectraMax Plus plate reader at 600 nm, using wells A12, B12 to blank.

The lowest concentration of NOVO3 without any cell growth is the MIC (Minimal Inhibitory Concentration) of NOVO3. The data shows the MIC of NOVO3 on different bacterial test strains in the presence of Mueller Hinton broth (MHB) or with MHB supplemented with either 0.05% BSA or with 0.02% Tween 80. The results show that the MIC is lowered significantly by the presence of either bovine serum albumin or Tween 80. While not being bound to any particular theory, this results may be due to a small amount of NOVO3 sticking to the plastic materials used in the experiment; thereby the MIC in MHB may be an underestimate, and NOVO3 may be even more potent than measured. The MIC data show that NOVO3 exhibit antibacterial activity against gram-positive bacteria.

TABLE 3

| | MIC (µg/ml) | | |
| --- | --- | --- | --- |
| Bacteria Strain | MHB | MHB + 0.05% BSA | MHB + 0.02% Tween 80 |
| B. subtilis 1A1 | 3 ± 1.3 | 0.166 ± 0.08 | 0.25 |
| MRSA NRS108 | 8 | 0.25 to 0.5 | |
| MSSA 29213 | 8 | 0.25 | |
| MSSA 33591 | 8 | 0.25 | |
| C. difficile 2001 | 32 | 8 | |
| C. difficile 196 | | 8 | |

Example 6

Effect of Serum on NOVO3 Activity

These studies follow the procedure for determining the MIC described above in Example 5. Briefly, two-fold serial dilution of the NOVO3 compound are added to the test cells of interest, MRSA and VRE, and the lowest concentration of compound that inhibits growth after a period of incubation is considered to be the MIC. To determine the effect of serum on the activity of NOVO3, MIC in the absence of serum is compared to MIC in media supplemented with varying concentrations (including 5%, 10%, 40%) of different sera including calf bovine serum (ATCC 30-2030), mouse serum (VWR 100181-200; tested at 10%), and human serum (VWR 12001-814; tested at 10%).

TABLE 4

| Bacteria Strain | MIC (μg/ml) | | | | |
|---|---|---|---|---|---|
| | MHB | MHB + 10% Calf Bovine Serum | MHB + 40% Calf Bovine Serum | MHB + 10% mouse serum | MHB + 10% human serum |
| B. subtilis 1A1 | 3 ± 1.3 | 0.144 ± −0.08 | 0.125 | 0.125 | 0.125 |

TABLE 4B

| Bacteria Strain | MIC (μg/ml) | | | |
|---|---|---|---|---|
| | MHB | MHB + 10% Calf Bovine Serum | MHB + 40% Calf Bovine Serum | GM* |
| MRSA NRS108 | 4 to 8 | 0.25 to 0.5 | 0.25 | 0.25 |

*is the growth media (Dulbecco's Modified Eagle's medium with 10% bovine calf serum) used to culture Mammalian cells NIH3T3

Example 7

Acute Toxicity Evaluation of NOVO3 in Mice

Groups of three female CD-1 mice are dosed with NOVO3 via the intravenous and subcutaneous routes in two administrations 3 hours apart. The mice are observed for 24 hours for acute toxicity/mortality. Blood is collected from the three mice via the subcutaneous route, processed to obtain plasma, frozen, and stored for analysis. Depending on the outcome of this dose, the procedure is repeated on an additional three mice per administration route at a lower dose level. Up to three doses are administered.

Example 8

Evaluation of the Efficacy of NOVO3 in a Systemic Infection Model in Mice

NOVO3 is evaluated for efficacy in the mouse systemic infection model against *S. aureus* (ATCC 13709). Mice in Groups 1-3 are inoculated with an IP injection of a suspension of the bacterium amended with 5% mucin. The following treatment groups are included:

TABLE 5

| Group | Treatment | Infected? | Dose (mg/kg) | Route | Schedule (hours after infection) | No. of Mice |
|---|---|---|---|---|---|---|
| 1 | Vehicle alone | Yes | N/A | i.v. | 1 & 4 | 6 |
| 2 | Ciprofloxacin | Yes | 2 | i.v. | 1 | 6 |
| 3 | NOVO3 | Yes | TBD | i.v. | 1 & 4 | 6 |
| 4 | NOVO3 | No | TBD | i.v. | 1 & 4 | 9 |

Mice are dosed with the vehicle (Group 1) or NOVO3 (Groups 3 and 4) at 1 hour and 4 hours after infection with *S. aureus*. Cumulative mortality counts are obtained for 6 days following infection and treatment.

Blood is collected from each of the three mice in Group 4 at 1 hour after the first dose and immediately before the second dose. The blood is processed to collect plasma. Samples are frozen and stored for analysis. The remaining three mice in this group are observed for 6 days following treatment for evaluation of drug tolerance.

Equivalents

Those skilled in the art will recognize, or be able to ascertain, using no more than routine experimentation, numerous equivalents to the specific embodiments described specifically herein. Such equivalents are intended to be encompassed in the scope of the following claims.

We claim:

1. A compound of formula I,

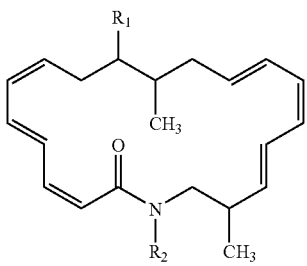

(I)

and an enantiomer, diastereomer, tautomer, or pharmaceutically-acceptable salt thereof, wherein:

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, (=O), $OR_a$, $OC(=O)R_a$, $SR_a$, $S(=O)_2R_d$, $NR_bR_c$ or sugar group;

$R_2$ is hydrogen, $NH_2$, —OH, alkyl or substituted alkyl, cycloalkyl or substituted cycloalkyl;

each $R_a$ is independently hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$ and $R_c$ are each independently hydrogen, alkyl, substituted alkyl, cycloalkyl, substituted cycloalkyl, heterocycle, substituted heterocycle, aryl, substituted aryl, or said $R_b$ and $R_c$ together with the N to which they are bonded optionally form a heterocycle or substituted heterocycle; and each $R_d$ is independently alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl.

2. The compound of claim 1, wherein $R_2$ is hydrogen.

3. The compound of claim 1, wherein $R_1$ is a sugar group.

4. The compound of claim 1 having the structure of Ia

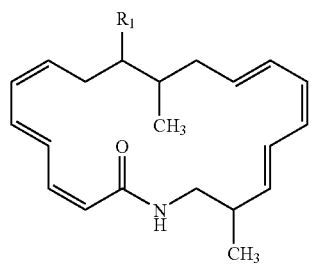

(Ia)

wherein $R_1$ is hydrogen, halogen, cyano, nitro, $CF_3$, $OCF_3$, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, (=O), $OR_a$, $OC(=O)R_a$, $SR_a$, $S(=O)_2R_d$, $NR_bR_c$ or sugar group.

5. The compound of claim 4, wherein $R_1$ is a sugar group.

6. The compound of claim 1 having the structure of Ib

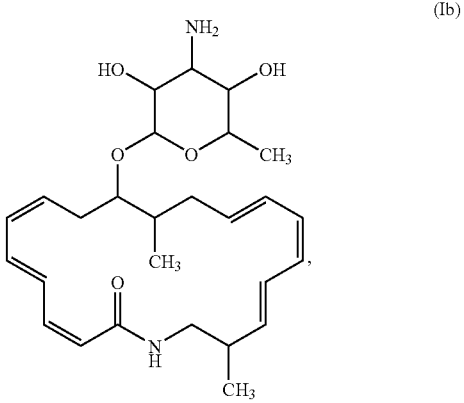

(Ib)

wherein the amino group is optionally mono-methylated, di-methylated, or acetylated, and wherein the hydroxyl group is optionally methylated or acetylated.

7. A compound of formula II,

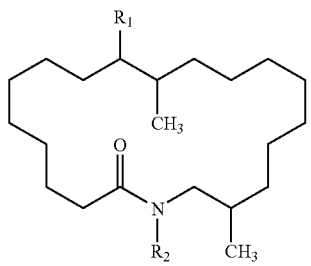

and an enantiomer, diastereomer, tautomer, or a pharmaceutically acceptable salt thereof, wherein:

$R_1$ is hydrogen, halogen, cyano, nitro, $CF_3$, $OCF_3$, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, (═O), $OR_a$, $OC(═O)R_a$, $SR_a$, $S(═O)_2R_d$, $NR_bR_c$ or sugar groups (including amino sugar and mono-, di- or polysaccharides);

$R_2$ is hydrogen, $NH_2$, —OH, alkyl, substituted alkyl, cycloalkyl, or substituted cycloalkyl;

each $R_a$ is independently hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl;

$R_b$ and $R_c$ are each independently hydrogen, alkyl, substituted alkyl, cycloalkyl, substituted cycloalkyl, heterocycle, substituted heterocycle, aryl, substituted aryl, or said $R_b$ and $R_c$ together with the N to which they are bonded optionally form a heterocycle or substituted heterocycle; and each $R_d$ is independently alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl.

8. The compound of claim 7, wherein $R_2$ is hydrogen.

9. The compound of claim 7, wherein $R_1$ is sugar group.

10. The compound of claim 7 having the structure of formula IIa:

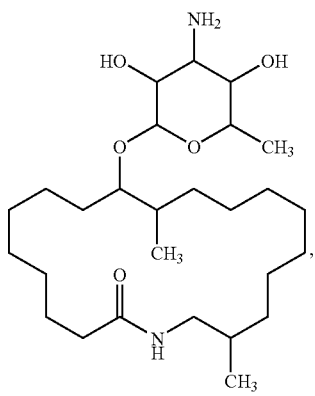

wherein the amino group optionally is mono-methylated, di-methylated, or acetylated, and wherein the hydroxyl group is optionally methylated or acetylated.

11. The compound of claim 1, further characterized by:
(a) a molecular weight of about 472.62 g/mol;
(b) a proton nuclear magnetic resonance spectrum substantially the same as that shown in FIG. 1; and
(c) a COSY nuclear magnetic resonance spectrum substantially the same as that shown in FIG. 2.

12. A pharmaceutical composition comprising the compound of claim 1 and a pharmaceutically-acceptable excipient, carrier, or diluent.

13. A pharmaceutical composition comprising the compound of claim 7 and a pharmaceutically-acceptable excipient, carrier, or diluent.

14. A method for producing a compound of formula Ib

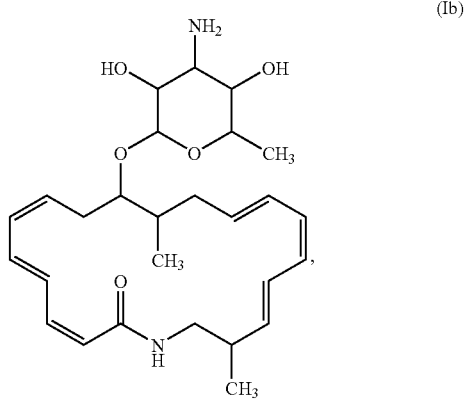

the method comprising cultivating a P1532 strain of *Streptosporangium* (ATCC Deposit No. PTA-8676) in a culture medium comprising assimilable sources of carbon, nitrogen, and inorganic salts under aerobic conditions enabling the production of an assayable amount of the compound of formula (Ib).

15. The method of claim 14, further comprising isolating the compound of formula (Ib).

16. A method of treating a disorder caused by Gram-positive bacteria in a subject in need thereof, the method comprising administering to the subject a therapeutically effective amount of a compound of formula (I),

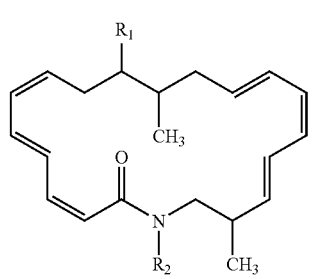

or an enantiomer, diastereomer, tautomer, or pharmaceutically acceptable salt thereof, wherein:

$R_1$ is hydrogen, halogen, cyano, nitro, $CF_3$, $OCF_3$, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, (=O), $OR_a$, $OC(=O)R_a$, $SR_a$, $S(=O)_2R_d$, $NR_bR_c$ or sugar group;

$R_2$ is hydrogen, $NH_2$, —OH, alkyl, substituted alkyl, cycloalkyl, or substituted cycloalkyl;

each $R_a$ is independently hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl;

$R_b$ and $R_c$ are each independently hydrogen, alkyl, substituted alkyl, cycloalkyl, substituted cycloalkyl, heterocycle, substituted heterocycle, aryl, substituted aryl, or said $R_b$ and $R_c$ together with the N to which they are bonded optionally form a heterocycle or substituted heterocycle; and each $R_d$ is independently alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl, wherein the administration of the compound treats the disorder of the mammal.

17. The method of claim 16, wherein the compound administered has the structure of formula (Ib),

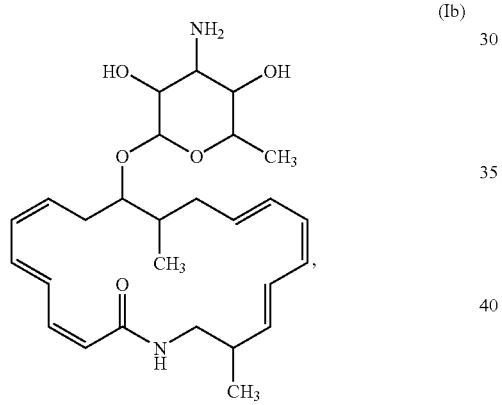

(Ib)

wherein the amino group is optionally mono-methylated, di-methylated, or acetylated, and wherein the hydroxyl group is optionally methylated or acetylated.

18. A method of inhibiting the growth of an infectious Gram-positive bacterial agent, the method comprising contact of contacting the agent with a compound of formula (I),

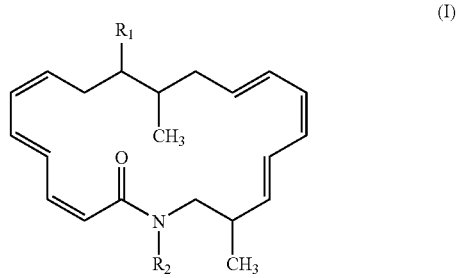

(I)

or an enantiomer, diastereomer, tautomer, or pharmaceutically-acceptable salt thereof, wherein:

$R_1$ is hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, (=O), $OR_a$, $OC(=O)R_a$, $SR_a$, $S(=O)_2R_d$, $NR_bR_c$ or sugar group;

$R_2$ is hydrogen, $NH_2$, —OH, alkyl or substituted alkyl, cycloalkyl or substituted cycloalkyl, (preferably hydrogen);

each $R_a$ is independently hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$ and $R_c$ are each independently hydrogen, alkyl, substituted alkyl, cycloalkyl, substituted cycloalkyl, heterocycle, substituted heterocycle, aryl, substituted aryl, or said $R_b$ and $R_c$ together with the N to which they are bonded optionally form a heterocycle or substituted heterocycle; and each $R_d$ is independently alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, or substituted aryl.

19. The method of claim 18, wherein the infectious agent is cultured in vitro.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agrgtttgat cctggctcag                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
tacggytacc ttgttacgac tt                                                22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
accagggtat ctaatcctgt                                                   20
```